US012807726B2

(12) United States Patent
Yang et al.

(10) Patent No.: US 12,807,726 B2
(45) Date of Patent: Nov. 24, 2026

(54) CD40 AGONISTIC ANTIBODY AND METHOD OF USE

(71) Applicant: WUXI BIOLOGICS (SHANGHAI) CO. LTD., Shanghai (CN)

(72) Inventors: Baotian Yang, Shanghai (CN); Jin Li, Shanghai (CN); Yong Zheng, Shanghai (CN)

(73) Assignee: WUXI BIOLOGICS (SHANGHAI) CO. LTD., Shanghai (CN)

( * ) Notice: Subject to any disclaimer, the term of this patent is extended or adjusted under 35 U.S.C. 154(b) by 899 days.

(21) Appl. No.: 18/021,382

(22) PCT Filed: Aug. 20, 2021

(86) PCT No.: PCT/CN2021/113679
§ 371 (c)(1),
(2) Date: Feb. 14, 2023

(87) PCT Pub. No.: WO2022/037662
PCT Pub. Date: Feb. 24, 2022

(65) Prior Publication Data

US 2023/0348609 A1 Nov. 2, 2023

(30) Foreign Application Priority Data

Aug. 21, 2020 (WO) ................ PCT/CN2020/110536

(51) Int. Cl.
*C07K 16/28* (2006.01)
*A61P 35/00* (2006.01)
*A61K 39/00* (2006.01)

(52) U.S. Cl.
CPC .......... *C07K 16/2878* (2013.01); *A61P 35/00* (2018.01); *A61K 2039/505* (2013.01);
(Continued)

(58) Field of Classification Search
None
See application file for complete search history.

(56) References Cited

U.S. PATENT DOCUMENTS

| | | | | |
|---|---|---|---|---|
| 10,577,425 B2 * | 3/2020 | Ellmark | ............. | C07K 16/2878 |
| 2012/0121585 A1 | 5/2012 | Heusser et al. | | |

(Continued)

FOREIGN PATENT DOCUMENTS

| | | |
|---|---|---|
| CN | 106554414 A | 4/2017 |
| CN | 108373505 A | 8/2018 |

(Continued)

OTHER PUBLICATIONS

OmniAb, OmniRat® & OmniFlic®: Transgenic rodents for human antibody discovery, Retrieved onine from <URL: https://www.omniab.com/technology/omnirat/> [retrieved on Nov. 25, 2025], 2025.*

(Continued)

*Primary Examiner* — Claire Kaufman
(74) *Attorney, Agent, or Firm* — James S. Keddie; Bozicevic, Field & Francis LLP

(57) ABSTRACT

Provided are anti-CD40 agonistic antibodies, the nucleic acid molecules encoding the anti-CD40 antibodies, expression vectors and host cells used for the expression of anti-CD40 antibodies. Further provided are the methods for validating the function of antibodies in vitro and the efficacy of antibodies in vivo. The antibodies provide a very potent agent for the treatment of cancers via modulating immune functions.

20 Claims, 9 Drawing Sheets

Specification includes a Sequence Listing.

(52) U.S. Cl.
CPC ...... *C07K 2317/33* (2013.01); *C07K 2317/52* (2013.01); *C07K 2317/732* (2013.01); *C07K 2317/75* (2013.01)

(56) References Cited

U.S. PATENT DOCUMENTS

| | | | |
|---|---|---|---|
| 2012/0263732 | A1 | 10/2012 | Gladue et al. |
| 2014/0004131 | A1 | 1/2014 | Mueller et al. |
| 2014/0205602 | A1 | 7/2014 | Long et al. |
| 2018/0066053 | A1 | 3/2018 | Keler et al. |
| 2019/0153111 | A1 | 5/2019 | Espie et al. |
| 2019/0202917 | A1 | 7/2019 | Campbell et al. |
| 2020/0079861 | A1 | 3/2020 | Wilson et al. |
| 2022/0081485 | A1 | 3/2022 | Liu et al. |

FOREIGN PATENT DOCUMENTS

| | | | |
|---|---|---|---|
| WO | WO 02/088186 | A1 | 11/2002 |
| WO | WO 03/040170 | A2 | 5/2003 |
| WO | WO 2005/063289 | A1 | 7/2005 |
| WO | WO 2012/149356 | A2 | 11/2012 |
| WO | WO 2017/184619 | A2 | 10/2017 |
| WO | WO 2018/085734 | A1 | 5/2018 |
| WO | WO 2018/115859 | A1 | 6/2018 |
| WO | WO 2019/198019 | A1 | 10/2019 |

OTHER PUBLICATIONS

Joyce et al., Comparisons of the antibody repertoires of a humanized rodent and humans by high throughput sequencing, Nature Res.Sci. Rep. 10:1120, 9 pages, Jan. 24, 2020.*

Ellmark et al., Modulation of the CD40-CD40 ligand interaction using human anti-CD40 single-chain antibody fragments obtained from the n-CoDeR phage display library, Immnol. 106(4):456-463, 2002.*

Li et al., Characteristics and clinical trial results of agonistic anti-CD40 antibodies in the treatment of malignancies (Review), Oncology Lett. 20:176, 13 pages, 2020.*

MacCallum et al., Antibody-antigen interactions: contact analysis and binding site topography, J. Mol. Biol. 262:732-745, 1996.*

Notice of Reasons for Refusal, issued for Japanese Application No. 2023-512310, mailed on Jun. 30, 2025.

Argiriadi et al., "CD40/anti-CD40 antibody complexes which illustrate agonist and antagonist structural switches", BMC Molecular and Cell Biology, 2019, 20:29, 13 pages.

Beatty et al., "Cancer immunotherapy: activating innate and adaptive immunity through CD40 agonists", Expert Rev Anticancer Ther., Feb. 2017, 17(2): 175-186.

The extended European search report for European Application No. 21857750.0, issued on Jul. 23, 2024.

* cited by examiner

Antibodies binding to human CD40 engineered cells

Antibodies binding to Raji cells

Antibodies binding to A431 cells

Antibodies binding to cynomolgus monkey CD40

Antibodies competition for CD40L and CD40 binding

CD40 homologous protein binding

Cross-species CD40 binding

NFκB reporter assay based on Ramos cells

| Antibody | EC50 (nM) |
|---|---|
| W3525-1.9.16-P5-uIgG2K | 1.4 |
| WBP352-BMK4.hIgG2K | 0.16 |
| WBP352-BMK5.hIgG1K | 0.96 |
| Human IgG1 | NA |
| Human IgG2 | NA |

NFκB reporter assay based on U937 cells

| Antibody | EC50 (nM) |
|---|---|
| W3525-1.9.16-P5-uIgG2K | 1.3 |
| WBP352-BMK4.hIgG2K | 0.81 |
| WBP352-BMK5.hIgG1K | 0.37 |
| Human IgG1 | NA |
| Human IgG2 | NA |

B cell proliferation assay

| Antibody | EC50 (nM) |
|---|---|
| W3525-1.9.16-P5-uIgG2K | 0.16 |
| WBP352-BMK4.hIgG2K | 0.16 |
| WBP352-BMK5.hIgG1K | 0.20 |
| Human IgG1 | NA |
| Human IgG2 | NA |

IL-12p40 secretion in *in vitro* DC activation assay

| Antibody | EC50 (nM) |
|---|---|
| W3525-1.9.16-P5-uIgG2K | 0.47 |
| WBP352-BMK4.hIgG2K | 1.2 |
| WBP352-BMK5.hIgG1K | 0.35 |
| Human IgG1 | NA |
| Human IgG2 | NA |

CD80 expression in *in vitro* DC activation assay

| Antibody | EC50 (nM) |
|---|---|
| W3525-1.9.16-P5-uIgG2K | 0.37 |
| WBP352-BMK4.hIgG2K | 0.88 |
| WBP352-BMK5.hIgG1K | 0.35 |
| Human IgG1 | NA |
| Human IgG2 | NA |

CD86 expression in *in vitro* DC activation assay

| Antibody | EC50 (nM) |
|---|---|
| W3525-1.9.16-P5-uIgG2K | 0.56 |
| WBP352-BMK4.hIgG2K | 0.88 |
| WBP352-BMK5.hIgG1K | NA |
| Human IgG1 | NA |
| Human IgG2 | NA |

CD54 expression in *in vitro* DC activation assay

CD83 expression in *in vitro* DC activation assay

ADCC effect of antibodies on human B cells

CD40 AGONISTIC ANTIBODY AND METHOD OF USE

CROSS REFERENCE

This application is a § 371 national phase of International Application No. PCT/CN2021/113679, filed on Aug. 20, 2021, which claims priority to International Patent Application No. PCT/CN2020/110536, filed on Aug. 21, 2020, the entire contents of which applications are incorporated herein by reference.

INCORPORATION BY REFERENCE OF SEQUENCE LISTING PROVIDED AS A TEXT FILE

A Sequence Listing is provided herewith in a text file, "CCPIT-041_SEQUENCE_LISTING.txt", created on Aug. 20, 2021, and having a size of 12,818 bytes. The contents of the text file are incorporated herein by reference in its entirety.

FIELD

This application generally relates to antibodies. More specifically, the application relates to fully human monoclonal antibodies against CD40, a method for preparing the same, and the use of the antibodies.

BACKGROUND

Immune checkpoint blockade (anti-CTLA-4, PD-1, and PD-L1 mAbs) offers the potential for durable remissions for patients across a broad range of cancers, including the most common ones (e.g. lung, breast cancer). Yet despite this broad applicability, the majority (well over 80%) of cancer patients is refractory to the therapy or become resistant to it[1]. Tumor necrosis factor receptor superfamily, member 5 (TNFRSF5, a.k.a. CD40), one of the immune-checkpoint proteins, plays an important role in regulating T cell immunity through activation of antigen presenting cells (APCs). CD40 is expressed on a wide range of hematopoietic (dendritic cells, B cells, monocytes)[4-6] and non-hematopoietic cells[7-8]. The interaction of CD40 on APCs, and its ligand CD40L expressed on activated effector T cells[9] results in APC licensing, which up-regulates cytokines production, antigen-presenting molecules, co-stimulatory molecules, and adhesion molecules[10-11]. Moreover, CD40 is a proximal regulator of other TNF family signaling receptors on T cells[12-13]. CD40 signaling results in the production of IL-12 and the up-regulation of CD70, CD86, OX40 ligand, 4-1BB ligand and GITR ligand on APCs. Stimulation of the corresponding receptors on $CD8^+$ T cells, in combination with IL-12 and type I IFNs, results in robust $CD8^+$ T cell activation, proliferation and effector function, as well as the formation and maintenance of tumor-specific $CD8^+$ T cell memory[14].

It was shown in several preclinical mouse tumor model and clinical trials that agonistic CD40 is quite a promising strategy for treating cancer. Multiple agonistic agents targeting CD40 have been developed by pharmaceutical companies, such as Pfizer, Roche, Abbvie and Apexigen. The agonistic CD40 antibody (CP-870,893, currently called selicrelumab or R07009789), developed by Pfizer, is a fully human IgG2 antibody that strongly activates dendritic cells and prime T cells to secrete IFN-γ[15]. CP-870,893 has shown clinical efficacy in patients with advanced cancer, either alone or in combination with other drugs, such as gemcitabine and anti-CTLA-4 antibody tremelimumab[16-18]. Apexigen is also developing a CD40 agonist, APX005M, an Fc-mutated humanized IgG1 monoclonal antibody. In an interim analysis of a small phase 1b study, 20 of 24 (83%) evaluable patients with metastatic pancreatic ductal adenocarcinoma demonstrated tumor shrinkage following treatment with APX005M in combination with gemcitabine and nab-paclitaxel with or without the anti-PD-1 antibody nivolumab[19]. CellDex's CD40 antibody, CDX-1140, which has lower level of agonistic activity than CP-870,893 but potent anti-tumor activity in xenograft models, is currently in phase 1 trial to determine the maximum tolerated dose and further evaluate its tolerability and efficacy[20]; furthermore, Alligator's ADC-1013 was collaborated with J&J for the potential treatment of advanced solid tumors.

There are some spaces for improvement for antibodies against CD40 as a therapeutic agent. As an agonistic antibody against co-stimulatory receptors, toxicity may be the most concerned question, such as cytokine release syndrome, which limits the clinical applications. For the strongest agonist tested, CP-870,893, the most common side effect is cytokine release syndrome, manifesting as chills, fever, rigors, and other symptoms soon after infusion. In the combination studies of APX005M with nivolumab, 54% patients (13 of 24) experienced an adverse event leading to discontinuation of the therapy, and 10 (42%) patients experienced a treatment-related serious adverse event[19]. Two dose-limiting toxicities, grade 3 and 4 febrile neutropenia, were observed during the treatment.

In the present disclosure, fully human antibodies against CD40, which not only have proper agonistic activity on CD40 pathway but also manifest a minimal safety risk, have been generated. The antibodies of the present disclosure can bind to human CD40 protein with high affinity; show weak or no ADCC effect and stimulate much lower cytokine release than CP-870,893; and effectively modulates immune responses in vitro and in vivo.

SUMMARY

These and other objectives are provided for by the present disclosure which, in a broad sense, is directed to compounds, methods, compositions and articles of manufacture that provide antibodies with improved efficacy. The benefits provided by the present disclosure are broadly applicable in the field of antibody therapeutics and diagnostics and may be used in conjunction with antibodies that react with a variety of targets.

The present disclosure provides antibodies against CD40, nucleic acid molecules encoding the anti-CD40 antibodies, expression vectors and host cells used for the expression of anti-CD40 antibodies, and methods for validating the function of antibodies in vitro and in vivo. The antibodies of the present disclosure provide a very potent agent for the treatment of multiple cancers via modulating human immune function.

In some aspects, the present disclosure comprises an isolated antibody, or an antigen-binding portion thereof against CD40, such as human CD40 or cynomolgus monkey CD40.

Preferably, the isolated antibody or an antigen-binding portion thereof have an agonistic activity on CD40.

In some embodiments, the isolated antibody or the antigen-binding portion thereof comprises:

(A) one or more heavy chain CDRs (HCDRs) selected from the group consisting of:

(i) a HCDR1 comprising SEQ ID NO: 1;
(ii) a HCDR2 comprising SEQ ID NO: 2; and
(iii) a HCDR3 comprising SEQ ID NO: 3;

(B) one or more light chain CDRs (LCDRs) selected from the group consisting of:
(i) a LCDR1 comprising SEQ ID NO: 7 or a variant thereof;
(ii) a LCDR2 comprising SEQ ID NO: 5; and
(iii) a LCDR3 comprising SEQ ID NO: 6; or (C) one or more HCDRs of (A) and one or more LCDRs of (B).

In some embodiments, the variant of SEQ ID NO: 7 comprises substitutions at no more than two amino acid positions in SEQ ID NO: 7, preferably one amino acid position in SEQ ID NO: 7. In some further embodiments, the substitution occurs at one of the three amino acids "NNG" in SEQ ID NO: 7. In at least one embodiment, the variant of SEQ ID NO: 7 is as set forth in SEQ ID NO: 4, which differs from SEQ ID NO: 7 by one amino acid substitution of "G" to "A" in "NNG".

In some embodiments, the isolated antibody or the antigen-binding portion thereof comprises:

(A) one or more heavy chain CDRs (HCDRs) selected from the group consisting of:
(i) a HCDR1 as set forth in SEQ ID NO: 1;
(ii) a HCDR2 as set forth in SEQ ID NO: 2; and
(iii) a HCDR3 as set forth in SEQ ID NO: 3;

(B) one or more light chain CDRs (LCDRs) selected from the group consisting of:
(i) a LCDR1 as set forth in SEQ ID NO: 4 or 7;
(ii) a LCDR2 as set forth in SEQ ID NO: 5; and
(iii) a LCDR3 as set forth in SEQ ID NO: 6; or (C) one or more HCDRs of (A) and one or more LCDRs of (B).

In some embodiments, the isolated antibody or the antigen-binding portion thereof comprises a heavy chain variable region (VH) and a light chain variable region (VL), wherein the VH comprises:
(i) a HCDR1 as set forth in SEQ ID NO: 1;
(ii) a HCDR2 as set forth in SEQ ID NO: 2; and
(iii) a HCDR3 as set forth in SEQ ID NO: 3; and the VL comprises:
(i) a LCDR1 as set forth in SEQ ID NO: 4 or 7;
(ii) a LCDR2 as set forth in SEQ ID NO: 5; and
(iii) a LCDR3 as set forth in SEQ ID NO: 6.

In some embodiments, the isolated antibody or the antigen-binding portion thereof comprises:

(A) a heavy chain variable region (VH):
(i) comprising the amino acid sequence as set forth in SEQ ID NO: 8;
(ii) comprising an amino acid sequence at least 85%, 90%, or 95% identical to the amino acid sequence as set forth in SEQ ID NO: 8; or
(iii) comprising an amino acid sequence with addition, deletion and/or substitution of one or more amino acids compared with the amino acid sequence as set forth in SEQ ID NO: 8; and/or (B) a light chain variable region (VL):
(i) comprising the amino acid sequence as set forth in SEQ ID NO: 9 or 10;
(ii) comprising an amino acid sequence at least 85%, at least 90%, or at least 95% identical to the amino acid sequence as set forth in SEQ ID NO: 9 or 10; or
(iii) comprising an amino acid sequence with addition, deletion and/or substitution of one or more amino acids compared with the amino acid sequence as set forth in SEQ ID NO: 9 or 10.

In some embodiments, the isolated antibody or the antigen-binding portion thereof comprises a heavy chain variable region comprising the amino acid sequence as set forth in SEQ ID NO: 8 and a light chain variable region as set forth in SEQ ID NO: 9 or 10.

In some embodiments, the isolated antibody or the antigen-binding portion thereof comprises a heavy chain variable region as set forth in SEQ ID NO: 8 and a light chain variable region as set forth in SEQ ID NO: 9 or 10.

In some embodiments, the isolated antibody or the antigen-binding portion thereof as disclosed herein further comprises a human IgG constant domain. The human IgG constant domain can be a human IgG1 or IgG2 constant domain, preferably a human IgG2 constant domain.

In some embodiments, the isolated antibodies or the antigen-binding portion thereof as disclosed herein has one or more of the following properties:

(a) strongly bind to cell surface human CD40 or cyno CD40 with an EC50 comparable to or better than the reference antibodies, as determined by FACS;
(b) specifically bind to human CD40, without cross-reactivity to human OX40, 4-1BB, GITR and BCMA;
(c) effectively compete with human CD40L for binding to CD40 with an IC50 at nM grade and about 100% inhibition rate;
(d) induce a concentration-dependent activation of NFκB and effectively enhance B cell proliferation in a dose-dependent manner, and both effects are more moderate than BMK4 (i.e. CP-870,893);
(e) induce moderate level of IL-12p40 secretion as well as CD80 and CD86 up-regulation;
(f) do not or weakly mediate ADCC activity on human B cells, e.g. CD40 positive B cells;
(g) do not stimulate human PBMC to release cytokines IL-2, IL-4, IL-6, IL-10, TNF, IFN-γ and IL-17A in great quantities; and
(h) have significant anti-tumor activity while well tolerated in the treated mice at all dose levels.

In some embodiments, the isolated antibody or the antigen-binding portion thereof as disclosed herein is a chimeric antibody, a humanized antibody or a fully human antibody. Preferably, the antibody is a fully human monoclonal antibody.

In some embodiments, the isolated antibody or the antigen-binding portion thereof as disclosed herein comprises a heavy chain with the amino acid sequence of SEQ ID No: 14, and a light chain with the amino acid sequence of SEQ ID No: 15.

In some aspects, the present disclosure is directed to an isolated nucleic acid molecule, comprising a nucleic acid sequence encoding the heavy chain variable region and/or the light chain variable region of the isolated antibody as disclosed herein.

In some aspects, the present disclosure is directed to a vector comprising the nucleic acid molecule encoding the antibody or antigen-binding portion thereof as disclosed herein.

In some aspects, the present disclosure is directed to a host cell comprising the expression vector as disclosed herein.

In some aspects, the present disclosure is directed to a pharmaceutical composition comprising at least one antibody or antigen-binding portion thereof as disclosed herein and a pharmaceutically acceptable carrier.

In some aspects, the present disclosure is directed to a method for preparing an anti-CD40 antibody or antigen-binding portion thereof which comprises expressing the antibody or antigen-binding portion thereof in the host cell and isolating the antibody or antigen-binding portion thereof from the host cell.

In some aspects, the present disclosure is directed to a method of modulating an CD40-related immune response in a subject, comprising administering the antibody or antigen-binding portion thereof as disclosed herein to the subject such that the CD40-related immune response in the subject is modulated.

In some aspects, the present disclosure is directed to a method for inhibiting growth of tumor cells in a subject, comprising administering an effective amount of the antibody or antigen-binding portion thereof or the pharmaceutical composition as disclosed herein to the subject.

In some aspects, the present disclosure is directed to a method for treating or preventing cancer in a subject comprising administering an effective amount of the antibody or antigen-binding portion thereof or the pharmaceutical composition as disclosed herein to the subject. In some embodiments, said cancer can be selected from breast cancer, lung cancer, colon cancer, ovarian cancer, melanoma, bladder cancer, renal cell carcinoma, liver cancer, prostate cancer, stomach cancer, pancreatic cancer, NSCLC, non-Hodgkin's lymphoma, chronic lymphocytic leukemia, diffuse large B-cell lymphoma, and multiple myeloma. In one embodiment, said cancer is colon cancer. In some other embodiments, said cancer is melanoma.

In some aspects, the present disclosure is directed to the use of the antibody or antigen-binding portion thereof as disclosed herein in the manufacture of a medicament for treating or preventing cancer.

In some aspects, the present disclosure is directed to the antibody or antigen-binding portion thereof as disclosed herein for use in treating or preventing cancer.

In some aspects, the present disclosure is directed to kits or devices and associated methods that employ the antibody or antigen-binding portion thereof as disclosed herein, and pharmaceutical compositions as disclosed herein.

The foregoing is a summary and thus contains, by necessity, simplifications, generalizations, and omissions of detail; consequently, those skilled in the art will appreciate that the summary is illustrative only and is not intended to be in any way limiting. Other aspects, features, and advantages of the methods, compositions and/or devices and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

DETAILED DESCRIPTION

Figure 1:
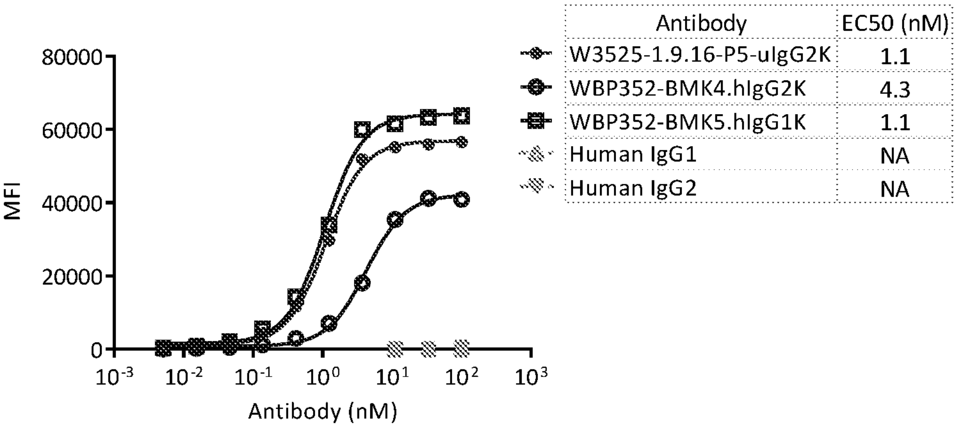
FIGS. 1-3 illustrate the binding result of W3525-1.9.16-P5-uIgG2K on human CD40 engineering cells (FIG. 1), Raji cells (FIG. 2) and A431 cells (FIG. 3) by FACS.

While the present disclosure may be embodied in many different forms, disclosed herein are specific illustrative embodiments thereof that exemplify the principles of the disclosure. It should be emphasized that the present disclosure is not limited to the specific embodiments illustrated. Moreover, any section headings used herein are for organizational purposes only and are not to be construed as limiting the subject matter described.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. More specifically, as used in this specification and the appended claims, the singular forms "a," "an" and "the" include plural referents unless the context clearly dictates otherwise. Thus, for example, reference to "a protein" includes a plurality of proteins; reference to "a cell" includes mixtures of cells, and the like. In this application, the use of "or" means "and/or" unless stated otherwise. Furthermore, the use of the term "comprising," as well as other forms, such as "comprises" and "comprised," is not limiting. In addition, ranges provided in the specification and appended claims include both end points and all points between the end points.

Generally, nomenclature used in connection with, and techniques of, cell and tissue culture, molecular biology, immunology, microbiology, genetics and protein and nucleic acid chemistry and hybridization described herein are those well-known and commonly used in the art. The methods and techniques of the present disclosure are generally performed according to conventional methods well known in the art and as described in various general and more specific references that are cited and discussed throughout the present specification unless otherwise indicated. See, e.g., Abbas et al., *Cellular and Molecular Immunology,* $6^{th}$ ed., W.B. Saunders Company (2010); Sambrook J. & Russell D.

*Molecular Cloning: A Laboratory Manual,* 3rd ed., Cold Spring Harbor Laboratory Press, Cold Spring Harbor, N.Y. (2000); Ausubel et al., *Short Protocols in Molecular Biology: A Compendium of Methods from Current Protocols in Molecular Biology*, Wiley, John & Sons, Inc. (2002); Harlow and Lane *Using Antibodies: A Laboratory Manual*, Cold Spring Harbor Laboratory Press, Cold Spring Harbor, N.Y. (1998); and Coligan et al., *Short Protocols in Protein Science*, Wiley, John & Sons, Inc. (2003). The nomenclature used in connection with, and the laboratory procedures and techniques of, analytical chemistry, synthetic organic chemistry, and medicinal and pharmaceutical chemistry described herein are those well-known and commonly used in the art.

Definitions

In order to better understand the disclosure, the definitions and explanations of the relevant terms are provided as follows.

The term "antibody" or "Ab," as used herein, generally refers to a Y-shaped tetrameric protein comprising two heavy (H) and two light (L) polypeptide chains held together by covalent disulfide bonds and non-covalent interactions. Light chains of an antibody may be classified into κ and λ light chain. Heavy chains may be classified into μ, δ, γ, α and ε, which define isotypes of an antibody as IgM, IgD, IgG, IgA and IgE, respectively. In a light chain and a heavy chain, a variable region is linked to a constant region via a "J" region of about 12 or more amino acids, and a heavy chain further comprises a "D" region of about 3 or more amino acids. Each heavy chain consists of a heavy chain variable region ($V_H$) and a heavy chain constant region ($C_H$). A heavy chain constant region consists of 3 domains ($C_H1$, $C_H2$ and $C_H3$). Each light chain consists of a light chain variable region ($V_L$) and a light chain constant region ($C_L$). $V_H$ and $V_L$ region can further be divided into hypervariable regions (called complementary determining regions (CDR)), which are interspaced by relatively conservative regions (called framework region (FR)). Each $V_H$ and $V_L$ consists of 3 CDRs and 4 FRs in the following order: FR1, CDR1, FR2, CDR2, FR3, CDR3, FR4 from N-terminal to C-terminal. The variable region (VH and VL) of each heavy/light chain pair forms antigen binding sites, respectively. Distribution of amino acids in various regions or domains follows the definition in Kabat Sequences of Proteins of Immunological Interest (National Institutes of Health, Bethesda, Md. (1987 and 1991)), or Chothia & Lesk (1987) J. Mol. Biol. 196: 901-917; Chothia et al., (1989) Nature 342:878-883. Antibodies may be of different antibody isotypes, for example, IgG (e.g., IgG1, IgG2, IgG3 or IgG4 subtype), IgA1, IgA2, IgD, IgE or IgM antibody.

The term "antigen-binding portion" or "antigen-binding fragment" of an antibody, which can be interchangeably used in the context of the application, refers to polypeptides comprising fragments of a full-length antibody, which retain the ability of specifically binding to an antigen that the full-length antibody specifically binds to, and/or compete with the full-length antibody for binding to the same antigen. Generally, see Fundamental Immunology, Ch. 7 (Paul, W., ed., the second edition, Raven Press, N.Y. (1989), which is incorporated herein by reference for all purposes. Antigen binding fragments of an antibody may be produced by recombinant DNA techniques or by enzymatic or chemical cleavage of an intact antibody. Under some conditions, antigen binding fragments include Fab, Fab', $F(ab')_2$, Fd, Fv, dAb and complementary determining region (CDR) fragments, single chain antibody (e.g. scFv), chimeric antibody, diabody and such polypeptides that comprise at least part of antibody sufficient to confer the specific antigen binding ability on the polypeptides. Antigen binding fragments of an antibody may be obtained from a given antibody (e.g., the monoclonal anti-human CD40 antibody provided in the instant application) by conventional techniques known by a person skilled in the art (e.g., recombinant DNA technique or enzymatic or chemical cleavage methods), and may be screened for specificity in the same manner by which intact antibodies are screened.

The term "monoclonal antibody" or "mAb," as used herein, refer to a preparation of antibody molecules of single molecular composition. A monoclonal antibody displays a binding specificity and affinity for a particular antigen.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "recombinant antibody," as used herein, refers to an antibody that is prepared, expressed, created or isolated by recombinant means, such as antibodies isolated from an animal that is transgenic for another species' immunoglobulin genes, antibodies expressed using a recombinant expression vector transfected into a host cell, antibodies isolated from a recombinant, combinatorial antibody library, or antibodies prepared, expressed, created or isolated by any other means that involves splicing of immunoglobulin gene sequences to other DNA sequences.

The term "fully human" as used herein, with reference to antibody or antigen-binding domain, means that the antibody or the antigen-binding domain has or consists of amino acid sequence(s) corresponding to that of an antibody produced by a human or a human immune cell, or derived from a non-human source such as a transgenic non-human animal that utilizes human antibody repertoires or other human antibody-encoding sequences. In certain embodiments, a fully human antibody does not comprise amino acid residues (in particular antigen-binding residues) derived from a non-human antibody.

The term "CD40", "CD40 antigen" or "CD40 protein", which are used interchangeably herein, is a single chain glycoprotein that is known to be a member of the tumor necrosis factor/nerve growth factor superfamily. CD40 is expressed by antigen-presenting cells (e.g. B cells, macrophages and DCs), as well as non-immune cells and tumors. CD40L is a natural ligand for CD40 and a Type II, 39-kDa membrane glycoprotein. CD40-CD40L is a pair of costimulatory molecules, and their interaction has been found to be essential in mediating a broad variety of immune and inflammatory responses including T cell-dependent immunoglobulin class switching, memory B cell development, and germinal center formation.

The term "anti-CD40 antibody" or "CD40 antibody" or "antibody against CD40," as used herein, refers to an antibody, as defined herein, capable of binding to a CD40, for example, a human CD40 protein. In certain embodiments, the anti-CD40 antibody as disclosed herein is an agonist of CD40.

The term "agonist" or "agonistic" includes any molecule that enhances or stimulates a biological activity of a native sequence peptide. Suitable agonist molecules specifically include agonist peptides, agonist antibodies or antibody fragments, fragments or amino acid sequence variants of native peptides, and the like. The term "CD40 agonist" refers to a molecule capable of stimulating, activating, or otherwise enhancing the activities of CD40, e.g., by binding to CD40 and stimulating CD40 activity, or by binding to one or more CD40 inhibitors and preventing interaction of the inhibitor with CD40. Agonists include, but are not limited to, antibodies and antigen-binding fragments thereof, proteins, peptides, glycoproteins, glycopeptides, glycolipids, polysaccharides, oligosaccharides, nucleic acids, bioorganic molecules, peptidomimetics, pharmacological agents and their metabolites, small molecules, fusion proteins, receptor molecules and derivatives, as well as antisense molecules, RNA aptamers, and ribozymes directed to a CD40 inhibitor.

The term "Ka," as used herein, is intended to refer to the association rate of a particular antibody-antigen interaction, whereas the term "Kd" as used herein, is intended to refer to the dissociation rate of a particular antibody-antigen interaction. Kd values for antibodies can be determined using methods well established in the art. The term "$K_D$" as used herein, is intended to refer to the dissociation constant of a particular antibody-antigen interaction, which is obtained from the ratio of Kd to Ka (i.e., Kd/Ka) and is expressed as a molar concentration (M). A preferred method for determining the Kd of an antibody is by using surface plasmon resonance, preferably using a biosensor system such as a Biacore® system.

The term "high affinity" for an IgG antibody, as used herein, refers to an antibody having a KD of $1\times10^{-7}$ M or less, more preferably $5\times10^{-8}$ M or less, even more preferably $1\times10^{-8}$ M or less for a target antigen, for example, CD40.

The term "$EC_{50}$," as used herein, which is also termed as "half maximal effective concentration" refers to the concentration of a drug, antibody or toxicant which induces a response halfway between the baseline and maximum after a specified exposure time. In the context of the application, $EC_{50}$ is expressed in the unit of "nM".

The ability of "block binding," as used herein, refers to the ability of an antibody or antigen-binding fragment thereof to block or inhibit the binding of two molecules to any detectable level. In certain embodiments, the binding between CD40 and CD40L can be inhibited at least 50% by the antibody or antigen-binding fragment thereof as disclosed herein. In certain embodiments, such an inhibitory effect may be greater than 60%, greater than 70%, greater than 80%, or greater than 90%.

The term "isolated," as used herein, refers to a state obtained from natural state by artificial means. If a certain "isolated" substance or component is present in nature, it is possible because its natural environment changes, or the substance is isolated from natural environment, or both. For example, a certain un-isolated polynucleotide or polypeptide naturally exists in a certain living animal body, and the same polynucleotide or polypeptide with a high purity isolated from such a natural state is called isolated polynucleotide or polypeptide. The term "isolated" excludes neither the mixed artificial or synthesized substance nor other impure substances that do not affect the activity of the isolated substance.

The term "isolated antibody," as used herein, is intended to refer to an antibody that is substantially free of other antibodies having different antigenic specificities (e.g., an isolated antibody that specifically binds a CD40 protein is substantially free of antibodies that specifically bind antigens other than CD40 proteins). An isolated antibody that specifically binds a human CD40 protein may, however, have cross-reactivity to other antigens, such as CD40 proteins from other species. Moreover, an isolated antibody can be substantially free of other cellular material and/or chemicals.

The term "vector," as used herein, refers to a nucleic acid vehicle which can have a polynucleotide inserted therein. When the vector allows for the expression of the protein encoded by the polynucleotide inserted therein, the vector is called an expression vector. The vector can have the carried genetic material elements expressed in a host cell by transformation, transduction, or transfection into the host cell. Vectors are well known by a person skilled in the art, including, but not limited to plasmids, phages, cosmids, artificial chromosome such as yeast artificial chromosome (YAC), bacterial artificial chromosome (BAC) or P1-derived artificial chromosome (PAC); phage such as λ phage or M13 phage and animal virus. The animal viruses that can be used as vectors, include, but are not limited to, retrovirus (including lentivirus), adenovirus, adeno-associated virus, herpes virus (such as herpes simplex virus), pox virus, baculovirus, papillomavirus, papova virus (such as SV40). A vector may comprise multiple elements for controlling expression, including, but not limited to, a promoter sequence, a transcription initiation sequence, an enhancer sequence, a selection element and a reporter gene. In addition, a vector may comprise origin of replication.

The term "host cell," as used herein, refers to a cellular system which can be engineered to generate proteins, protein fragments, or peptides of interest. Host cells include, without limitation, cultured cells, e.g., mammalian cultured cells derived from rodents (rats, mice, guinea pigs, or hamsters) such as CHO, BHK, NSO, SP2/0, YB2/0; or human tissues or hybridoma cells, yeast cells, and insect cells, and cells comprised within a transgenic animal or cultured tissue. The term encompasses not only the particular subject cell but also the progeny of such a cell. Because certain modifications may occur in succeeding generations due to either mutation or environmental influences, such progeny may not be identical to the parent cell, but are still included within the scope of the term "host cell".

The term "identity," as used herein, refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al, 1988, SIAMJ. Applied Math. 48:1073.

The term "immunogenicity," as used herein, refers to ability of stimulating the formation of specific antibodies or sensitized lymphocytes in organisms. It not only refers to the property of an antigen to stimulate a specific immunocyte to activate, proliferate and differentiate so as to finally generate immunologic effector substance such as antibody and sensitized lymphocyte, but also refers to the specific immune response that antibody or sensitized T lymphocyte can be formed in immune system of an organism after stimulating the organism with an antigen. Immunogenicity is the most important property of an antigen. Whether an antigen can successfully induce the generation of an immune response in a host depends on three factors, properties of an antigen, reactivity of a host, and immunization means.

The term "transfection," as used herein, refers to the process by which nucleic acids are introduced into eukaryotic cells, particularly mammalian cells. Protocols and techniques for transfection include but not limited to lipid transfection and chemical and physical methods such as electroporation. A number of transfection techniques are well known in the art and are disclosed herein. See, e.g., Graham et al., 1973, Virology 52:456; Sambrook et al., 2001, Molecular Cloning: A Laboratory Manual, supra; Davis et al., 1986, Basic Methods in Molecular Biology, Elsevier; Chu et al, 1981, Gene 13:197. In a specific embodiment of the disclosure, human CD40 gene was transfected into 293F cells.

The term "hybridoma" and the term "hybridoma cell line," as used herein, may be used interchangeably. When the term "hybridoma" and the term "hybridoma cell line" are mentioned, they also include subclone and progeny cell of hybridoma.

The term "SPR" or "surface plasmon resonance," as used herein, refers to and includes an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 5 and Jönsson, U., et al. (1993) *Ann. Biol. Clin.* 51:19-26; Jönsson, U., et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

The term "fluorescence-activated cell sorting" or "FACS," as used herein, refers to a specialized type of flow cytometry. It provides a method for sorting a heterogeneous mixture of biological cells into two or more containers, one cell at a time, based upon the specific light scattering and fluorescent characteristics of each cell (FlowMetric. "Sorting Out Fluorescence Activated Cell Sorting". Retrieved 2017-11-09). Instruments for carrying out FACS are known to those of skill in the art and are commercially available to the public. Examples of such instruments include FACS Star Plus, FACScan and FACSort instruments from Becton Dickinson (Foster City, Calif.) Epics C from Coulter Epics Division (Hialeah, Fla.) and MoFlo from Cytomation (Colorado Springs, Colo.).

The term "antibody-dependent cell-mediated cytotoxicity" or "ADCC," as used herein, refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. PNAS (USA) 95:652-656 (1998).

The term "subject" includes any human or nonhuman animal, preferably humans.

The term "cancer," as used herein, refers to any tumor or a malignant cell growth, proliferation or metastasis-mediated, solid tumors and non-solid tumors such as leukemia and initiate a medical condition.

The term "treatment," "treating" or "treated," as used herein in the context of treating a condition, pertains generally to treatment and therapy, whether of a human or an animal, in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included. For cancer, "treating" may refer to dampen or slow the tumor or malignant cell growth, proliferation, or metastasis, or some combination thereof. For tumors, "treatment" includes removal of all or part of the tumor, inhibiting or slowing tumor growth and metastasis, preventing or delaying the development of a tumor, or some combination thereof.

The term "an effective amount," as used herein, pertains to that amount of an active compound, or a material, composition or dosage form comprising an active compound, which is effective for producing some desired therapeutic effect, commensurate with a reasonable benefit/risk ratio, when administered in accordance with a desired treatment regimen. For instance, the "an effective amount," when used in connection with treatment of CD40-related diseases or conditions, refers to an antibody or antigen-binding portion thereof in an amount or concentration effective to treat the said diseases or conditions.

The term "prevent," "prevention" or "preventing," as used herein, with reference to a certain disease condition in a mammal, refers to preventing or delaying the onset of the disease, or preventing the manifestation of clinical or subclinical symptoms thereof.

The term "pharmaceutically acceptable," as used herein, means that the vehicle, diluent, excipient and/or salts thereof, are chemically and/or physically is compatible with other ingredients in the formulation, and the physiologically compatible with the recipient.

As used herein, the term "a pharmaceutically acceptable carrier and/or excipient" refers to a carrier and/or excipient pharmacologically and/or physiologically compatible with a subject and an active agent, which is well known in the art (see, e.g., Remington's Pharmaceutical Sciences. Edited by Gennaro A R, 19th ed. Pennsylvania: Mack Publishing Company, 1995), and includes, but is not limited to pH adjuster, surfactant, adjuvant and ionic strength enhancer. For example, the pH adjuster includes, but is not limited to, phosphate buffer; the surfactant includes, but is not limited to, cationic, anionic, or non-ionic surfactant, e.g., Tween-80; the ionic strength enhancer includes, but is not limited to, sodium chloride.

As used herein, the term "adjuvant" refers to a non-specific immunopotentiator, which can enhance immune response to an antigen or change the type of immune response in an organism when it is delivered together with the antigen to the organism or is delivered to the organism in advance. There are a variety of adjuvants, including, but not limited to, aluminium adjuvants (for example, aluminum hydroxide), Freund's adjuvants (for example, Freund's complete adjuvant and Freund's incomplete adjuvant), coryne bacterium parvum, lipopolysaccharide, cytokines, and the like. Freund's adjuvant is the most commonly used adjuvant in animal experiments now. Aluminum hydroxide adjuvant is more commonly used in clinical trials.

Anti-CD40 Antibodies

In some aspects, the disclosure comprises an isolated antibody or an antigen-binding portion thereof against CD40.

In the context of the application, the "antibody" may include polyclonal antibodies, multiclonal antibodies, monoclonal antibodies, chimeric antibodies, humanized and primatized antibodies, CDR grafted antibodies, human antibodies, recombinantly produced antibodies, intrabodies, multispecific antibodies, bispecific antibodies, monovalent antibodies, multivalent antibodies, anti-idiotypic antibodies, synthetic antibodies, including muteins and variants thereof; and derivatives thereof including Fc fusions and other modifications, and any other immune-reactive molecule so long as it exhibits preferential association or binding with a CD40 protein. Moreover, unless dictated otherwise by contextual constraints the term further comprises all classes of antibodies (i.e. IgA, IgD, IgE, IgG, and IgM) and all subclasses (i.e., IgG1, IgG2, IgG3, IgG4, IgA1, and IgA2). In a preferred embodiment, the antibody is a monoclonal antibody. In a more preferred embodiment, the antibody is a humanized monoclonal antibody or fully human monoclonal antibody.

Monoclonal antibodies can be prepared using a wide variety of techniques known in the art including hybridoma techniques, recombinant techniques, phage display technologies, transgenic animals (e.g., a XenoMouse®) or some combination thereof. For example, monoclonal antibodies can be produced using hybridoma and art-recognized biochemical and genetic engineering techniques such as described in more detail in An, Zhigiang (ed.) *Therapeutic Monoclonal Antibodies: From Bench to Clinic*, John Wiley and Sons, 1st ed. 2009; Shire et. al. (eds.) *Current Trends in Monoclonal Antibody Development and Manufacturing*, Springer Science+Business Media LLC, 1st ed. 2010; Harlow et al., *Antibodies: A Laboratory Manual*, Cold Spring Harbor Laboratory Press, 2nd ed. 1988; Hammerling, et al., in: *Monoclonal Antibodies and T-Cell Hybridomas* 563-681 (Elsevier, N.Y., 1981) each of which is incorporated herein in its entirety by reference. In some embodiments, the antibody as disclosed herein is obtained by utilizing hybridoma technology and genetically engineered rat OMNIRAT™ (developed by Open Monoclonal Technology (OMT) Company[2-3]). It should be understood that a selected binding sequence can be further altered, for example, to improve affinity for the target, to humanize the target binding sequence, to improve its production in cell culture, to reduce its immunogenicity in vivo, to create a multi-specific antibody, etc., and that an antibody comprising the altered target binding sequence is also an antibody of this disclosure.

In a preferred embodiment, the anti-human CD40 monoclonal antibody is prepared by using hybridoma techniques. Generation of hybridomas is well-known in the art. See, e.g., Harlow and Lane (1988) Antibodies, A Laboratory Manual, Cold Spring Harbor Publications, New York.

In this application, a series of high-throughput screening is performed for identifying the positive hybridoma cell lines. The goal of the screening process is to find candidate human and cyno CD40 high affinity binders with suitable functional activity on the CD40 pathway. The sequences of the antibodies are further optimized (e.g. PTM removal) to obtain a lead antibody with high binding affinity and suitable agonistic activity.

Anti-CD40 Agonistic Antibodies

Although antagonistic anti-CD40 antibodies have been developed, it has been found that agonistic CD40 is quite a promising strategy for treating cancer. Multiple agonistic agents targeting CD40 are in clinical trials, such as CP-870, 893 (Pfizer), APX005M (Apexigen), CDX-1140 (CellDex), and ADC-1013 (Alligator), which are all agonistic CD40 antibodies.

In cancer treatment, the main mechanism of CD40-agonistic antibodies is to license APC to induce anti-tumor T cell response, not requiring CD40 expression on the tumor cells. CD40-agonistic antibodies can substitute for CD40L on activated T cells to boost immunity. CD40-activated B cells enter into a proliferation state which in turn enhance the T-cell response.

As demonstrated in the Examples, the anti-CD40 antibodies as disclosed herein can effectively enhance B cell proliferation (in vitro proliferation assay), can induce a concentration-dependent activation of NFκB (RGA assay), and induce much lower levels of cytokines production, such as IL-2, IL-4, IL-6 and TNF compared to reference antibodies. Therefore, the anti-CD40 antibodies as disclosed herein have a much lower risk of causing cytokine release syndrome (CRS), which is the most frequently reported adverse event for an agonistic anti-CD40 antibody in clinical trials.

Anti-CD40 Antibodies with Certain Properties

The antibodies of the present disclosure are characterized by particular functional features or properties of the antibodies. The in vitro functional characteristics and pharmacological activity of the antibodies have been fully assessed at the molecular and cellular levels according to the mechanism of action for the target. In some embodiments, the isolated antibodies or the antigen-binding portion thereof have one or more of the following properties:

(a) strongly bind to cell surface human CD40 or cynomolgus monkey CD40 with an EC50 comparable to or better than the reference antibodies;
(b) effectively compete with human CD40L for binding to CD40 with an IC50 of 1.4 nM and 100% inhibition rate;
(c) specifically bind to human CD40, without cross-reactivity to human OX40, 4-1BB, GITR and BCMA;
(d) show cross-reactivity to human and cynomolgus monkey CD40, but no cross-reactivity to mouse, rat and canine CD40;
(e) induce a concentration-dependent activation of NFκB, and is demonstrated to be at a more moderate magnitude than BMK4;
(f) effectively enhance B cell proliferation in a dose-dependent manner, and the effect is more moderate than that of BMK4;
(g) induce moderate level of IL-12p40 secretion, as well as CD80 and CD86 up-regulation;
(h) in human IgG2 format, do not or weakly mediate ADCC activity on human B cells;
(i) do not stimulate human PBMC to release cytokines IL-2, IL-4, IL-6, IL-10, TNF, IFN-γ and IL-17A in great quantities; and
(j) have significant anti-tumor activity and are well tolerated in the treated mice at all dose levels.

The antibody of the disclosure binds to both human and cynomolgus monkey CD40 with high affinity. The binding of an antibody of the disclosure to CD40 can be assessed using one or more techniques well established in the art, for instance, ELISA. The binding specificity of an antibody of the disclosure can also be determined by monitoring binding of the antibody to cells expressing an CD40 protein, e.g., flow cytometry. For example, an antibody can be tested by a flow cytometry assay in which the antibody is reacted with a cell line that expresses human CD40, such as CHO K1 cells that have been transfected to express CD40 on their cell surface. Additionally, or alternatively, the binding of the antibody, including the binding kinetics (e.g., $K_d$ value) can be tested in BIAcore binding assays. Still other suitable binding assays include ELISA assays, for example using a recombinant CD40 protein. For instance, an antibody of the disclosure binds to a human CD40 with a $K_D$ of 10 nM or less, binds to a human CD40 with a $K_D$ of 9.5 nM or less, binds to a human CD40 with a $K_D$ of 9 nM or less, binds to a human CD40 protein with a $K_D$ of 8.5 nM or less, binds to a human CD40 protein with a $K_D$ of 8 nM or less, binds to a human CD40 protein with a $K_D$ of 7.5 nM or less, or binds to a human CD40 protein with a $K_D$ of 7 nM or less, as determined by BIAcore binding assays.

Further, the antibodies of the present disclosure may block the binding of CD40L to CD40. The CD40 ligand/CD40 pathway is widely recognized for its prominent role in immune regulation and homeostasis. The engagement of the CD40 and CD40 ligands, which are transiently expressed on T cells and other non-immune cells under inflammatory conditions, regulates a wide spectrum of molecular and cellular processes, including the initiation and progression of cellular and humoral adaptive immunity. The antibodies of the present disclosure have been shown to effectively compete with human CD40L for binding to CD40 with an IC50 at nM grade and about 100% inhibition rate.

Anti-CD40 Antibodies Comprising CDRs

In some embodiments, the isolated antibody or the antigen-binding portion thereof comprises:

A) one or more heavy chain CDRs (HCDRs) selected from the group consisting of:
(i) a HCDR1 comprising SEQ ID NO: 1;
(ii) a HCDR2 comprising SEQ ID NO: 2; and
(iii) a HCDR3 comprising SEQ ID NO: 3;

B) one or more light chain CDRs (LCDRs) selected from the group consisting of:
(i) a LCDR1 comprising SEQ ID NO: 7 or a variant thereof;
(ii) a LCDR2 comprising SEQ ID NO: 5; and
(iii) a LCDR3 comprising SEQ ID NO: 6; or C) one or more HCDRs of A) and one or more LCDRs of B).

In some embodiments, the variant of SEQ ID NO: 7 comprises substitutions at no more than two amino acid positions of SEQ ID NO: 7, preferably no more than one amino acid position of SEQ ID NO: 7. In some further embodiments, the substitution occurs at one of the amino acids “NNG” in SEQ ID NO: 7, for example by mutating amino acid “G” to any other amino acid. In one embodiment, the variant of SEQ ID NO: 7 is as set forth in SEQ ID NO: 4, which differs from SEQ ID NO: 7 by one amino acid substitution of “G” to “A” in “NNG”.

Variable regions and CDRs in an antibody sequence can be identified according to general rules that have been developed in the art (as set out above, such as, for example, the Kabat numbering system) or by aligning the sequences against a database of known variable regions. Methods for identifying these regions are described in Kontermann and Dubel, eds., Antibody Engineering, Springer, New York, NY, 2001 and Dinarello et al., Current Protocols in Immunology, John Wiley and Sons Inc., Hoboken, NJ, 2000. Exemplary databases of antibody sequences are described in, and can be accessed through, the “Abysis” website at www.bioinf.org.uk/abs (maintained by A.C. Martin in the Department of Biochemistry & Molecular Biology University College London, London, England) and the VBASE2 website at www.vbase2.org, as described in Retter et al., Nucl. Acids Res., 33 (Database issue): D671-D674 (2005). Preferably sequences are analyzed using the Abysis database, which integrates sequence data from Kabat, IMGT and the Protein Data Bank (PDB) with structural data from the PDB. See Dr. Andrew C. R. Martin's book chapter *Protein Sequence and Structure Analysis of Antibody Variable Domains*. In: *Antibody Engineering Lab Manual* (Ed.: Duebel, S. and Kontermann, R., Springer-Verlag, Heidelberg, ISBN-13: 978-3540413547, also available on the website bioinforg.uk/abs). The Abysis database website further includes general rules that have been developed for identifying CDRs which can be used in accordance with the teachings herein. Unless otherwise indicated, all CDRs set forth herein are derived according to Kabat numbering system.

In some embodiments, the isolated antibody or the antigen-binding portion thereof comprises:

A) one or more heavy chain CDRs (HCDRs) selected from at least one of the group consisting of:
(i) a HCDR1 as set forth in SEQ ID NO: 1;
(ii) a HCDR2 as set forth in SEQ ID NO: 2; and
(iii) a HCDR3 as set forth in SEQ ID NO: 3;

B) one or more light chain CDRs (LCDRs) selected from at least one of the group consisting of:
(i) a LCDR1 as set forth in SEQ ID NO: 4 or 7;
(ii) a LCDR2 as set forth in SEQ ID NO: 5; and
(iii) a LCDR3 as set forth in SEQ ID NO: 6; or C) one or more HCDRs of A) and one or more LCDRs of B).

In a specific embodiment, the isolated antibody or the antigen-binding portion thereof comprises a heavy chain variable region (VH) and a light chain variable region (VL), and wherein (a) the VH comprises:
(i) a HCDR1 as set forth in SEQ ID NO: 1;
(ii) a HCDR2 as set forth in SEQ ID NO: 2; and
(iii) a HCDR3 as set forth in SEQ ID NO: 3; and (b) the VL comprises:
(i) a LCDR1 as set forth in SEQ ID NO: 4 or 7;
(ii) a LCDR2 as set forth in SEQ ID NO: 5; and
(iii) a LCDR3 as set forth in SEQ ID NO: 6.

Anti-CD40 Antibodies Comprising a Heavy Chain Variable Region and a Light Chain Variable Region In some embodiments, the isolated antibody or the antigen-binding portion thereof comprises:

(A) a heavy chain variable region (VH):
(i) comprising the amino acid sequence as set forth in SEQ ID NO: 8;
(ii) comprising an amino acid sequence at least 85%, 90%, or 95% identical to the amino acid sequence as set forth in SEQ ID NO: 8; or
(iii) comprising an amino acid sequence with addition, deletion and/or substitution of one or more amino acids compared with the amino acid sequence as set forth in SEQ ID NO: 8; and/or (B) a light chain variable region:
(i) comprising the amino acid sequence as set forth in SEQ ID NO: 9 or 10;
(ii) comprising an amino acid sequence at least 85%, at least 90%, or at least 95% identical to the amino acid sequence as set forth in SEQ ID NO: 9 or 10; or
(iii) comprising an amino acid sequence with addition, deletion and/or substitution of one or more amino acids compared with the amino acid sequence as set forth in SEQ ID NO: 9 or 10.

The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present disclosure can further be used as a “query sequence” to perform a search against public databases to, for example, identify related sequences. Such searches can be performed using the XBLAST program (version 2.0) of Altschul, et al. (1990) J. MoI. Biol. 215:403-10. BLAST protein searches can be performed with the XBLAST program, score=50, wordlength=3 to obtain amino acid sequences homologous to the antibody molecules of the disclosure. To obtain gapped alignments for comparison purposes, Gapped BLAST can be utilized as described in Altschul et al, (1997) Nucleic Acids Res. 25(17):3389-3402. When utilizing BLAST and Gapped BLAST programs, the default parameters of the respective programs (e.g., XBLAST and NBLAST) can be used. See www.ncbi.nlm.nih.gov.

In a specific embodiment, the isolated antibody or the antigen-binding portion thereof comprises: a heavy chain variable region comprising or consisting of the amino acid sequence of SEQ ID NO: 8 and a light chain variable region comprising or consisting of the amino acid sequence of SEQ ID NO: 9 or 10.

In other embodiments, the amino acid sequences of the heavy chain variable region and/or the light chain variable region can be at least 85%, 86%, 87%, 88%, 89%, 90%, 91%, 92%, 93%, 94%, 95%, 96%, 97%, 98% or 99% identical to the respective sequences set forth above.

In some further embodiments, the isolated antibody or the antigen-binding portion thereof may contain conservative substitution or modification of amino acids in the variable regions of the heavy chain and/or light chain. It is understood in the art that certain conservative sequence modification can be made which do not remove antigen binding. See, e.g., Brummell et al. (1993) Biochem 32:1180-8; de Wildt et al. (1997) Prot. Eng. 10:835-41; Komissarov et al. (1997) J. Biol. Chem. 272:26864-26870; Hall et al. (1992) J. Immunol. 149:1605-12; Kelley and O’Connell (1993) Biochem. 32:6862-35; Adib-Conquy et al. (1998) Int. Immunol. 10:341-6 and Beers et al. (2000) Clin. Can. Res. 6:2835-43.

As described above, the term “conservative substitution,” as used herein, refers to amino acid substitutions which would not disadvantageously affect or change the essential properties of a protein/polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having alkaline side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having β-branched side chains (such as threonine, valine, isoleucine) and amino acids having aromatic side chains (for example, tyrosine, phenylalanine, tryptophan, histidine). Therefore, a corresponding amino acid residue is preferably substituted with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl. Acad. Sci. USA 94: 412-417 (1997), which are incorporated herein by reference).

IgG Constant Domain Comprising the Fc Region

The anti-CD40 antibodies and antigen-binding fragments provided herein further comprise a IgG constant domain, such as a human IgG constant domain. The human IgG constant domain may be a human IgG1 or IgG2 constant domain, preferably a human IgG2 constant domain. In some embodiments, the Fc region is a human IgG2 Fc region. For example, the Fc region may be a wild-type Fc region; alternatively, the Fc region may comprise one or more amino acid substitution(s) that alters the antibody-dependent cellular cytotoxicity (ADCC) or other effector functions.

Human IgG2 is the weakest isotype for FcγRIIB and FcγRIIIA binding, and it can elicit agonistic activity independent of Fc-mediated crosslinking, thus reducing the potential toxicity caused by super-clustering through the interaction of Fc and FcγRs. Moreover, one CD40L trimer interacts with two CD40 receptors naturally[24]. Similarly, the antibodies disclosed herein with human IgG2 backbone can cluster CD40 to form a dimer, to mimic the interaction between CD40L trimer and CD40.

As shown in the Examples, W3525-1.9.16-P5-uIgG2K and BMK4, which are in human IgG2 format, didn’t or weakly mediate ADCC activity on human B cells, therefore would not likely trigger ADCC on CD40 positive B cells. In contrast, BMK5, the Fc backbone of which is human IgG1, can induce ADCC effect effectively on human B cells in a dose-dependent manner.

Nucleic Acid Molecules Encoding Antibodies of the Disclosure

In some aspects, the disclosure is directed to an isolated nucleic acid molecule, comprising a nucleic acid sequence encoding the heavy chain variable region and/or the light chain variable region of the isolated antibody as disclosed herein.

Nucleic acids of the disclosure can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

The isolated nucleic acid encoding the VH region can be converted to a full-length heavy chain gene by operatively linking the VH-encoding nucleic acid to another DNA molecule encoding heavy chain constant regions (CH1, CH2 and CH3). The sequences of human heavy chain constant region genes are known in the art (see e.g., Kabat et al. (1991), supra) and DNA fragments encompassing these regions can be obtained by standard PCR amplification. The heavy chain constant region can be an IgG1, IgG2, IgG3, IgG4, IgA, IgE, IgM or IgD constant region, but more preferably is an IgG1 or IgG4 constant region.

The isolated nucleic acid encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat et al., supra) and DNA fragments encompassing these regions can be obtained by standard PCR amplification. In preferred embodiments, the light chain constant region can be a kappa or lambda constant region.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

Nucleic acid sequences encoding the heavy and light chain of the anti-CD40 antibody as described herein can be cloned into one expression vector, each nucleotide sequence being in operable linkage to a suitable promoter. In one embodiment, each of the nucleotide sequences encoding the heavy chain and light chain is in operable linkage to a distinct prompter. Alternatively, the nucleotide sequences encoding the heavy chain and the light chain can be in operable linkage with a single promoter, such that both heavy and light chains are expressed from the same promoter. When necessary, an internal ribosomal entry site (IRES) can be inserted between the heavy chain and light chain encoding sequences.

In some embodiments, the nucleotide sequences encoding the two chains of the antibody are cloned into two vectors, which can be introduced into the same or different cells. When the two chains are expressed in different cells, each of them can be isolated from the host cells expressing such and the isolated heavy chains and light chains can be mixed and incubated under suitable conditions allowing for the formation of the antibody.

In some embodiments, the disclosure is directed to an isolated nucleic acid molecule, comprising a nucleic acid sequence encoding the heavy chain variable region or heavy chain of the isolated antibody as disclosed herein.

In some specific embodiments, the isolated nucleic acid molecule encodes the heavy chain variable region of the isolated antibody and comprises a nucleic acid sequence selected from the group consisting of:

(A) a nucleic acid sequence that encodes a heavy chain variable region as set forth in SEQ ID NO: 8;

(B) a nucleic acid sequence as set forth in SEQ ID NO: 11; or (C) a nucleic acid sequence that hybridized under high stringency conditions to the complementary strand of the nucleic acid sequence of (A) or (B).

In some embodiments, the disclosure is directed to an isolated nucleic acid molecule, comprising a nucleic acid sequence encoding the light chain variable region or light chain of the isolated antibody as disclosed herein.

In some specific embodiments, the isolated nucleic acid molecule encodes the light chain variable region of the isolated antibody comprises a nucleic acid sequence selected from the group consisting of:

(A) a nucleic acid sequence that encodes a light chain variable region as set forth in SEQ ID NO: 9 or 10;

(B) a nucleic acid sequence as set forth in SEQ ID NO: 12 or 13; or (C) a nucleic acid sequence that hybridized under high stringency conditions to the complementary strand of the nucleic acid sequence of (A) or (B).

For example, the nucleic acid molecule is consisted of SEQ ID NO: 11, 12 or 13. Alternatively, the nucleic acid molecule shares at least 80% (e.g. at least 85%, 86%, 87%, 88%, 89%, 90%, 91%, 92%, 93%, 94%, 95%, 96%, 97%, 98%, or 99%) sequence identity to SEQ ID NO: 11, 12 or 13. In some specific embodiments, the percentage of identity is derived from the degeneracy of the genetic code, and the encoded protein sequences remain unchanged.

Exemplary high stringency conditions include hybridization at 45° C. in 5×SSPE and 45% formamide, and a final wash at 65° C. in 0.1×SSC. It is understood in the art that conditions of equivalent stringency can be achieved through variation of temperature and buffer, or salt concentration as described Ausubel, et al. (Eds.), Protocols in Molecular Biology, John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described in Sambrook, et al, (Eds.), Molecular Cloning: A laboratory Manual. Cold Spring Harbor Laboratory Press: Cold Spring Harbor, New York (1989), pp. 9.47 to 9.51.

Host Cells

Host cells as disclosed in the present disclosure may be any cell which is suitable for expressing the antibodies of the present disclosure, for instance, *E. coli* cells, yeast cells, insect cells, and mammalian cells. Mammalian host cells for expressing the antibodies of the present disclosure include Chinese Hamster Ovary (CHO cells) (including dhfr-CHO cells, described in Urlaub and Chasm, (1980) Proc. Natl. Acad. ScL USA 77:4216-4220, used with a DHFR selectable marker, e.g., as described in R. J. Kaufman and P. A. Sharp (1982) J. MoI. Biol. 159:601-621), NSO myeloma cells, COS cells and SP2 cells. In particular, for use with NSO myeloma cells, another expression system is the GS gene expression system disclosed in WO 87/04462, WO 89/01036 and EP 338,841. When recombinant expression vectors encoding the antibody are introduced into mammalian host cells, the antibodies are produced by culturing the host cells for a period of time sufficient to allow for expression of the antibody in the host cells or, secretion of the antibody into the culture medium in which the host cells are grown. Antibodies can be recovered from the culture medium using standard protein purification methods.

Pharmaceutical Compositions

In some aspects, the disclosure is directed to a pharmaceutical composition comprising at least one antibody or antigen-binding portion thereof as disclosed herein and a pharmaceutically acceptable carrier.

Components of the Compositions

The pharmaceutical composition may optionally contain one or more additional pharmaceutically active ingredients, such as another antibody or a drug. The pharmaceutical compositions of the disclosure also can be administered in a combination therapy with, for example, another immune-stimulatory agent, anti-cancer agent, an antiviral agent, or a vaccine, such that the anti-CD40 antibody enhances the immune response against the vaccine. A pharmaceutically acceptable carrier can include, for example, a pharmaceutically acceptable liquid, gel or solid carriers, an aqueous medium, a non-aqueous medium, an anti-microbial agent, isotonic agents, buffers, antioxidants, anesthetics, suspending/dispersing agent, a chelating agent, a diluent, adjuvant, excipient or a nontoxic auxiliary substance, other known in the art various combinations of components or more.

Suitable components may include, for example, antioxidants, fillers, binders, disintegrating agents, buffers, preservatives, lubricants, flavorings, thickening agents, coloring agents, emulsifiers or stabilizers such as sugars and cyclodextrin. Suitable anti-oxidants may include, for example, methionine, ascorbic acid, EDTA, sodium thiosulfate, platinum, catalase, citric acid, cysteine, mercapto glycerol, thioglycolic acid, Mercapto sorbitol, butyl methyl anisole, butylated hydroxy toluene and/or propylgalacte. As disclosed in the present disclosure, in a solvent containing an antibody or an antigen-binding fragment of the present disclosure discloses compositions include one or more anti-oxidants such as methionine, reducing antibody or antigen binding fragment thereof may be oxidized. The oxidation reduction may prevent or reduce a decrease in binding affinity, thereby enhancing antibody stability and extended shelf life. Thus, in some embodiments, the present disclosure provides a composition comprising one or more antibodies or antigen binding fragment thereof and one or more anti-oxidants such as methionine. The present disclosure further provides a variety of methods, wherein an antibody or antigen binding fragment thereof is mixed with one or more anti-oxidants, such as methionine, so that the antibody or antigen binding fragment thereof can be prevented from oxidation, to extend their shelf life and/or increased activity.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcelluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

Administration, Formulation and Dosage

The pharmaceutical composition of the disclosure may be administered in vivo, to a subject in need thereof, by various routes, including, but not limited to, oral, intravenous, intra-arterial, subcutaneous, parenteral, intranasal, intramuscular, intracranial, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. The appropriate formulation and route of administration may be selected according to the intended application and therapeutic regimen.

Suitable formulations for enteral administration include hard or soft gelatin capsules, pills, tablets, including coated tablets, elixirs, suspensions, syrups or inhalations and controlled release forms thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Similarly, the particular dosage regimen, including dose, timing and repetition, will depend on the particular individual and that individual's medical history, as well as empirical considerations such as pharmacokinetics (e.g., half-life, clearance rate, etc.).

Frequency of administration may be determined and adjusted over the course of therapy, and is based on reducing the number of proliferative or tumorigenic cells, maintaining the reduction of such neoplastic cells, reducing the proliferation of neoplastic cells, or delaying the development of metastasis. In some embodiments, the dosage administered may be adjusted or attenuated to manage potential side effects and/or toxicity. Alternatively, sustained continuous release formulations of a subject therapeutic composition may be appropriate.

It will be appreciated by one of skill in the art that appropriate dosages can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action that achieve the desired effect without causing substantial harmful or deleterious side-effects.

In general, the antibody or the antigen binding portion thereof of the disclosure may be administered in various ranges. These include about 5 μg/kg body weight to about 100 mg/kg body weight per dose; about 50 μg/kg body weight to about 5 mg/kg body weight per dose; about 100 μg/kg body weight to about 10 mg/kg body weight per dose. Other ranges include about 100 μg/kg body weight to about 20 mg/kg body weight per dose and about 0.5 mg/kg body weight to about 20 mg/kg body weight per dose. In certain embodiments, the dosage is at least about 100 μg/kg body weight, at least about 250 μg/kg body weight, at least about 750 μg/kg body weight, at least about 3 mg/kg body weight, at least about 5 mg/kg body weight, at least about 10 mg/kg body weight.

In any event, the antibody or the antigen binding portion thereof of the disclosure is preferably administered as needed to subjects in need thereof. Determination of the frequency of administration may be made by persons skilled in the art, such as an attending physician based on considerations of the condition being treated, age of the subject being treated, severity of the condition being treated, general state of health of the subject being treated and the like.

In certain preferred embodiments, the course of treatment involving the antibody or the antigen-binding portion thereof of the present disclosure will comprise multiple doses of the selected drug product over a period of weeks or months. More specifically, the antibody or the antigen-binding portion thereof of the present disclosure may be administered once every day, every two days, every four days, every week, every ten days, every two weeks, every three weeks, every month, every six weeks, every two months, every ten weeks or every three months. In this regard, it will be appreciated that the dosages may be altered or the interval may be adjusted based on patient response and clinical practices.

Dosages and regimens may also be determined empirically for the disclosed therapeutic compositions in individuals who have been given one or more administration(s). For example, individuals may be given incremental dosages of a therapeutic composition produced as described herein. In selected embodiments, the dosage may be gradually increased or reduced or attenuated based respectively on empirically determined or observed side effects or toxicity. To assess efficacy of the selected composition, a marker of the specific disease, disorder or condition can be followed as described previously. For cancer, these include direct measurements of tumor size via palpation or visual observation, indirect measurement of tumor size by x-ray or other imaging techniques; an improvement as assessed by direct tumor biopsy and microscopic examination of the tumor sample; the measurement of an indirect tumor marker (e.g., PSA for prostate cancer) or a tumorigenic antigen identified according to the methods described herein, a decrease in pain or paralysis; improved speech, vision, breathing or other disability associated with the tumor; increased appetite; or an increase in quality of life as measured by accepted tests or prolongation of survival. It will be apparent to one of skill in the art that the dosage will vary depending on the individual, the type of neoplastic condition, the stage of neoplastic condition, whether the neoplastic condition has begun to metastasize to other location in the individual, and the past and concurrent treatments being used.

Compatible formulations for parenteral administration (e.g., intravenous injection) will comprise the antibody or antigen-binding portion thereof as disclosed herein in concentrations of from about 10 μg/ml to about 100 mg/ml. In certain selected embodiments, the concentrations of the antibody or the antigen binding portion thereof will comprise 20 μg/ml, 40 μg/ml, 60 μg/ml, 80 μg/ml, 100 μg/ml, 200 μg/ml, 300, μg/ml, 400 μg/ml, 500 μg/ml, 600 μg/ml, 700 μg/ml, 800 μg/ml, 900 μg/ml or 1 mg/ml. In other preferred embodiments, the concentrations of the antibody or the antigen binding portion thereof will comprise 2 mg/ml, 3 mg/ml, 4 mg/ml, 5 mg/ml, 6 mg/ml, 8 mg/ml, 10 mg/ml, 12 mg/ml, 14 mg/ml, 16 mg/ml, 18 mg/ml, 20 mg/ml, 25 mg/ml, 30 mg/ml, 35 mg/ml, 40 mg/ml, 45 mg/ml, 50 mg/ml, 60 mg/ml, 70 mg/ml, 80 mg/ml, 90 mg/ml or 100 mg/ml Applications of the Disclosure The antibodies, antibody compositions and methods of the present disclosure have numerous in vitro and in vivo utilities involving, for example, detection of CD40 or enhancement of immune response. For example, these molecules can be administered to cells in culture, in vitro or ex vivo, or to human subjects, e.g., in vivo, to enhance immunity in a variety of situations. The immune response can be modulated, for instance, augmented, stimulated or up-regulated.

For instance, the subjects include human patients in need of enhancement of an immune response. The methods are particularly suitable for treating human patients having a disorder that can be treated by augmenting an immune response (e.g., the T-cell mediated immune response). In a particular embodiment, the methods are particularly suitable for treatment of cancer in vivo. To achieve antigen-specific enhancement of immunity, the anti-CD40 antibodies can be administered together with an antigen of interest or the antigen may already be present in the subject to be treated (e.g., a tumor-bearing or virus-bearing subject). When antibodies to CD40 are administered together with another agent, the two can be administered in either order or simultaneously.

The present disclosure further provides methods for detecting the presence of human CD40 antigen in a sample, or measuring the amount of human CD40 antigen, comprising contacting the sample, and a control sample, with a human monoclonal antibody, or an antigen binding portion thereof, which specifically binds to human CD40, under conditions that allow for formation of a complex between the antibody or portion thereof and human CD40. The formation of a complex is then detected, wherein a difference complex formation between the sample compared to the control sample is indicative of the presence of human CD40 antigen in the sample. Moreover, the anti-CD40 antibodies of the disclosure can be used to purify human CD40 via immunoaffinity purification.

Treatment of Disorders Including Cancers

In some aspects, the present disclosure provides a method of treating a disorder or a disease in a mammal, which comprises administering to the subject (for example, a human) in need of treatment a therapeutically effective amount of the antibody or antigen-binding portion thereof as disclosed herein. The disorder or disease may be a cancer.

A variety of cancers where CD40 is implicated, whether malignant or benign and whether primary or secondary, may be treated or prevented with a method provided by the disclosure. The cancers may be solid cancers or hematologic malignancies. Examples of such cancers include lung cancers such as bronchogenic carcinoma (e.g., non-small cell lung cancer, squamous cell carcinoma, small cell carcinoma, large cell carcinoma, and adenocarcinoma), alveolar cell carcinoma, bronchial adenoma, chondromatous hamartoma (noncancerous), and sarcoma (cancerous); heart cancer such as myxoma, fibromas, and rhabdomyomas; bone cancers such as osteochondromas, condromas, chondroblastomas, chondromyxoid fibromas, osteoid osteomas, giant cell tumors, chondrosarcoma, multiple myeloma, osteosarcoma, fibrosarcomas, malignant fibrous histiocytomas, Ewing's tumor (Ewing's sarcoma), and reticulum cell sarcoma; brain cancer such as gliomas (e.g., glioblastoma multiforme), anaplastic astrocytomas, astrocytomas, oligodendrogliomas, medulloblastomas, chordoma, Schwannomas, ependymomas, meningiomas, pituitary adenoma, pinealoma, osteomas, hemangioblastomas, craniopharyngiomas, chordomas, germinomas, teratomas, dermoid cysts, and angiomas; cancers in digestive system such as colon cancer, leiomyoma, epidermoid carcinoma, adenocarcinoma, leiomyosarcoma, stomach adenocarcinomas, intestinal lipomas, intestinal neurofibromas, intestinal fibromas, polyps in large intestine, and colorectal cancers; liver cancers such as hepatocellular adenomas, hemangioma, hepatocellular carcinoma, fibrolamellar carcinoma, cholangiocarcinoma, hepatoblastoma, and angiosarcoma; kidney cancers such as kidney adenocarcinoma, renal cell carcinoma, hypernephroma, and transitional cell carcinoma of the renal pelvis; bladder cancers; hematological cancers such as acute lymphocytic (lymphoblastic) leukemia, acute myeloid (myelocytic, myelogenous, myeloblasts, myelomonocytic) leukemia, chronic lymphocytic leukemia (e.g., Sezary syndrome and hairy cell leukemia), chronic myelocytic (myeloid, myelogenous, granulocytic) leukemia, Hodgkin's lymphoma, non-Hodgkin's lymphoma, B cell lymphoma, mycosis fungoides, and myeloproliferative disorders (including myeloproliferative disorders such as polycythemia vera, myelofibrosis, thrombocythemia, and chronic myelocytic leukemia); skin cancers such as basal cell carcinoma, squamous cell carcinoma, melanoma, Kaposi's sarcoma, and Paget's disease; head and neck cancers; eye-related cancers such as retinoblastoma and intraoccular melanocarcinoma; male reproductive system cancers such as benign prostatic hyperplasia, prostate cancer, and testicular cancers (e.g., seminoma, teratoma, embryonal carcinoma, and choriocarcinoma); breast cancer; female reproductive system cancers such as uterine cancer (endometrial carcinoma), cervical cancer (cervical carcinoma), cancer of the ovaries (ovarian carcinoma), vulvar carcinoma, vaginal carcinoma, fallopian tube cancer, and hydatidiform mole; thyroid cancer (including papillary, follicular, anaplastic, or medullary cancer); pheochromocytomas (adrenal gland); noncancerous growths of the parathyroid glands; pancreatic cancers; and hematological cancers such as leukemias, myelomas, non-Hodgkin's lymphomas, and Hodgkin's lymphomas. In a specific embodiment, the cancer is colon cancer. In another specific embodiment, the cancer is melanoma.

In some embodiments, examples of cancer include but not limited to B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; and post-transplant lymphoproliierative disorder (PTLD), as well as abnormal vascular proliferation associated with phakomatoses, edema (such as that associated with brain tumors), B-cell proliferative disorders, and Meigs' syndrome. More specific examples include, but are not limited to, relapsed or refractory NHL, front line low grade NHL, Stage III/IV NHL, chemotherapy resistant NHL, precursor B lymphoblastic leukemia and/or lymphoma, small lymphocytic lymphoma, B-cell chronic lymphocytic leukemia and/or prolymphocytic leukemia and/or small lymphocytic lymphoma, B-cell prolymphocytic lymphoma, immunocytoma and/or lymphoplasmacytic lymphoma, lymphoplasmacytic lymphoma, marginal zone B-cell lymphoma, splenic marginal zone lymphoma, extranodal marginal zone-MALT lymphoma, nodal marginal zone lymphoma, hairy cell leukemia, plasmacytoma and/or plasma cell myeloma, low grade/follicular lymphoma, intermediate grade/follicular NHL, mantle cell lymphoma, follicle center lymphoma (follicular), intermediate grade diffuse NHL, diffuse large B-cell lymphoma, aggressive NHL (including aggressive front-line NHL and aggressive relapsed NHL), NHL relapsing after or refractory to autologous stem cell transplantation, primary mediastinal large B-cell lymphoma, primary effusion lymphoma, high grade immunoblastic NHL, high grade lymphoblastic NHL, high grade small non-cleaved cell NHL, bulky disease NHL, Burkitt's lymphoma, precursor (peripheral) large granular lymphocytic leukemia, mycosis fungoides and/or Sezary syndrome, skin (cutaneous) lymphomas, anaplastic large cell lymphoma, angiocentric lymphoma.

In some embodiments, examples of cancer further include, but are not limited to, B-cell proliferative disorders, which further include, but are not limited to, lymphomas (e.g., B-Cell Non-Hodgkin's lymphomas (NHL)) and lymphocytic leukemias. Such lymphomas and lymphocytic leukemias include e.g. a) follicular lymphomas, b) Small Non-Cleaved Cell Lymphomas/Burkitt's lymphoma (including endemic Burkitt's lymphoma, sporadic Burkitt's lymphoma and Non-Burkitt's lymphoma), c) marginal zone lymphomas (including extranodal marginal zone B-cell lymphoma (Mucosa-associated lymphatic tissue lymphomas, MALT), nodal marginal zone B-cell lymphoma and splenic marginal zone lymphoma), d) Mantle cell lymphoma (MCL), e) Large Cell Lymphoma (including B-cell diffuse large cell lymphoma (DLCL), Diffuse Mixed Cell Lymphoma, Immunoblastic Lymphoma, Primary Mediastinal B-Cell Lymphoma, Angiocentric Lymphoma-Pulmonary B-Cell Lymphoma), f) hairy cell leukemia, g) lymphocytic lymphoma, Waldenstrom's macroglobulinemia, h) acute lymphocytic leukemia (ALL), chronic lymphocytic leukemia (CLL)/small lymphocytic lymphoma (SLL), B cell prolymphocytic leukemia, i) plasma cell neoplasms, plasma cell myeloma, multiple myeloma, plasmacytoma, and/or j) Hodgkin's disease.

Stimulation of an Immune Response

In some aspects, the disclosure also provides a method of enhancing (for example, stimulating) an immune response in a subject comprising administering an antibody or an antigen binding portion thereof of the disclosure to the subject such that an immune response in the subject is enhanced. For example, the subject is a mammal. In a specific embodiment, the subject is a human.

The term "enhancing an immune response" or its grammatical variations, means stimulating, evoking, increasing, improving, or augmenting any response of a mammal's immune system. The immune response may be a cellular response (i.e. cell-mediated, such as cytotoxic T lymphocyte mediated) or a humoral response (i.e. antibody mediated response), and may be a primary or secondary immune response. Examples of enhancement of immune response include increased $CD4^+$ helper T cell activity and generation of cytolytic T cells. The enhancement of immune response can be assessed using a number of in vitro or in vivo measurements known to those skilled in the art, including, but not limited to, cytotoxic T lymphocyte assays, release of cytokines (for example IL-2 production or IFN-γ production), regression of tumors, survival of tumor bearing animals, antibody production, immune cell proliferation, expression of cell surface markers, and cytotoxicity. Typically, methods of the disclosure enhance the immune response by a mammal when compared to the immune response by an untreated mammal or a mammal not treated using the methods as disclosed herein. In one embodiment, the immune response is cytokine production, particularly IFN-γ production or IL-12 production. In another embodiment, the immune response is enhanced B cell proliferation.

For an agonistic antibody against co-stimulatory receptors, toxicity such as cytokine release syndrome limits its clinical application. Thus, a moderate level of agonistic activity might be preferred in order not to elicit a high cytotoxicity or a high quantity of released cytokine. The antibodies as disclosed herein enhance IL-12 secretion and activation markers expression of DCs, but at a more moderate magnitude than BMK4.

The antibody or the antigen-binding portion thereof may be used alone as a monotherapy, or may be used in combination with chemical therapies or radiotherapies.

Combined Use with Chemotherapies

The antibody or the antigen-binding portion thereof may be used in combination with an anti-cancer agent, a cytotoxic agent or chemotherapeutic agent.

The term "anti-cancer agent" or "anti-proliferative agent" means any agent that can be used to treat a cell proliferative disorder such as cancer, and includes, but is not limited to, cytotoxic agents, cytostatic agents, anti-angiogenic agents, debulking agents, chemotherapeutic agents, radiotherapy and radiotherapeutic agents, targeted anti-cancer agents, BRMs, therapeutic antibodies, cancer vaccines, cytokines, hormone therapies, radiation therapy and anti-metastatic agents and immunotherapeutic agents. It will be appreciated that, in selected embodiments as discussed above, such anti-cancer agents may comprise conjugates and may be associated with the disclosed site-specific antibodies prior to administration. More specifically, in certain embodiments selected anti-cancer agents will be linked to the unpaired cysteines of the engineered antibodies to provide engineered conjugates as set forth herein. Accordingly, such engineered conjugates are expressly contemplated as being within the scope of the present disclosure. In other embodiments, the disclosed anti-cancer agents will be given in combination with site-specific conjugates comprising a different therapeutic agent as set forth above.

As used herein the term "cytotoxic agent" means a substance that is toxic to the cells and decreases or inhibits the function of cells and/or causes destruction of cells. In certain embodiments, the substance is a naturally occurring molecule derived from a living organism. Examples of cytotoxic agents include, but are not limited to, small molecule toxins or enzymatically active toxins of bacteria (e.g., Diptheria toxin, Pseudomonas endotoxin and exotoxin, Staphylococcal enterotoxin A), fungal (e.g., α-sarcin, restrictocin), plants (e.g., abrin, ricin, modeccin, viscumin, pokeweed anti-viral protein, saporin, gelonin, momoridin, trichosanthin, barley toxin, *Aleurites fordii* proteins, dianthin proteins, *Phytolacca mericana* proteins (PAPI, PAPII, and PAP-S), *Momordica charantia* inhibitor, curcin, crotin, *Saponaria officinalis* inhibitor, gelonin, mitegellin, restrictocin, phenomycin, neomycin, and the tricothecenes) or animals, (e.g., cytotoxic RNases, such as extracellular pancreatic RNases; DNase I, including fragments and/or variants thereof).

For the purposes of the present disclosure a "chemotherapeutic agent" comprises a chemical compound that non-specifically decreases or inhibits the growth, proliferation, and/or survival of cancer cells (e.g., cytotoxic or cytostatic agents). Such chemical agents are often directed to intracellular processes necessary for cell growth or division, and are thus particularly effective against cancerous cells, which generally grow and divide rapidly. For example, vincristine depolymerizes microtubules, and thus inhibits cells from entering mitosis. In general, chemotherapeutic agents can include any chemical agent that inhibits, or is designed to inhibit, a cancerous cell or a cell likely to become cancerous or generate tumorigenic progeny (e.g., TIC). Such agents are often administered, and are often most effective, in combination, e.g., in regimens such as CHOP or FOLFIRI.

Examples of anti-cancer agents that may be used in combination with the site-specific constructs of the present disclosure (either as a component of a site specific conjugate or in an unconjugated state) include, but are not limited to, alkylating agents, alkyl sulfonates, aziridines, ethylenimines and methylamelamines, acetogenins, a camptothecin, bryostatin, callystatin, CC-1065, cryptophycins, dolastatin, duocarmycin, eleutherobin, pancratistatin, a sarcodictyin, spongistatin, nitrogen mustards, antibiotics, enediyne antibiotics, dynemicin, bisphosphonates, esperamicin, chromoprotein enediyne antibiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, erlotinib, vemurafenib, crizotinib, sorafenib, ibrutinib, enzalutamide, folic acid analogues, purine analogs, androgens, anti-adrenals, folic acid replenisher such as frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, an epothilone, etoglucid, gallium nitrate, hydroxyurea, lentinan, lonidainine, maytansinoids, mitoguazone, mitoxantrone, mopidanmol, nitraerine, pentostatin, phenamet, pirarubicin, losoxantrone, podophyllinic acid, 2-ethylhydrazide, procarbazine, PSK® polysaccharide complex (JHS Natural Products, Eugene, OR), razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, chloranbucil; GEMZAR® gemcitabine; 6-thioguanine; mercaptopurine; methotrexate; platinum analogs, vinblastine; platinum; etoposide (VP-16);

ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11), topoisomerase inhibitor RFS 2000; difluorometlhylornithine; retinoids; capecitabine; combretastatin; leucovorin; oxaliplatin; inhibitors of PKC-alpha, Raf, H-Ras, EGFR and VEGF-A that reduce cell proliferation and pharmaceutically acceptable salts, acids or derivatives of any of the above. Also included in this definition are anti-hormonal agents that act to regulate or inhibit hormone action on tumors such as anti-estrogens and selective estrogen receptor modulators, aromatase inhibitors that inhibit the enzyme aromatase, which regulates estrogen production in the adrenal glands, and anti-androgens; as well as troxacitabine (a 1,3-dioxolane nucleoside cytosine analog); antisense oligonucleotides, ribozymes such as a VEGF expression inhibitor and a HER2 expression inhibitor; vaccines, PROLEUKIN® rIL-2; LURTOTECAN® topoisomerase 1 inhibitor; ABARELIX® rmRH; Vinorelbine and Esperamicins and pharmaceutically acceptable salts, acids or derivatives of any of the above.

Combined Use with Radiotherapies

The present disclosure also provides for the combination of the antibody or the antigen-binding portion thereof with radiotherapy (i.e., any mechanism for inducing DNA damage locally within tumor cells such as gamma-irradiation, X-rays, UV-irradiation, microwaves, electronic emissions and the like). Combination therapy using the directed delivery of radioisotopes to tumor cells is also contemplated, and the disclosed antibodies may be used in connection with a targeted anti-cancer agent or other targeting means. Typically, radiation therapy is administered in pulses over a period of time from about 1 to about 2 weeks. The radiation therapy may be administered to subjects having head and neck cancer for about 6 to 7 weeks. Optionally, the radiation therapy may be administered as a single dose or as multiple, sequential doses.

Diagnosis

The disclosure provides in vitro and in vivo methods for detecting, diagnosing or monitoring proliferative disorders and methods of screening cells from a patient to identify tumor cells including tumorigenic cells. Such methods include identifying an individual having cancer for treatment or monitoring progression of a cancer, comprising contacting the patient or a sample obtained from a patient (either in vivo or in vitro) with an antibody as described herein and detecting presence or absence, or level of association, of the antibody to bound or free target molecules in the sample. In some embodiments, the antibody will comprise a detectable label or reporter molecule as described herein.

In some embodiments, the association of the antibody with particular cells in the sample can denote that the sample may contain tumorigenic cells, thereby indicating that the individual having cancer may be effectively treated with an antibody as described herein.

Samples can be analyzed by numerous assays, for example, radioimmunoassays, enzyme immunoassays (e.g. ELISA), competitive-binding assays, fluorescent immunoassays, immunoblot assays, Western Blot analysis and flow cytometry assays. Compatible in vivo theragnostic or diagnostic assays can comprise art recognized imaging or monitoring techniques, for example, magnetic resonance imaging, computerized tomography (e.g. CAT scan), positron tomography (e.g., PET scan), radiography, ultrasound, etc., as would be known by those skilled in the art.

Pharmaceutical Packs and Kits

Pharmaceutical packs and kits comprising one or more containers, comprising one or more doses of the antibody or the antigen-binding portion thereof are also provided. In certain embodiments, a unit dosage is provided wherein the unit dosage contains a predetermined amount of a composition comprising, for example, the antibody or the antigen-binding portion thereof, with or without one or more additional agents. For other embodiments, such a unit dosage is supplied in single-use prefilled syringe for injection. In still other embodiments, the composition contained in the unit dosage may comprise saline, sucrose, or the like; a buffer, such as phosphate, or the like; and/or be formulated within a stable and effective pH range. Alternatively, in certain embodiments, the composition may be provided as a lyophilized powder that may be reconstituted upon addition of an appropriate liquid, for example, sterile water or saline solution. In certain preferred embodiments, the composition comprises one or more substances that inhibit protein aggregation, including, but not limited to, sucrose and arginine. Any label on, or associated with, the container(s) indicates that the enclosed conjugate composition is used for treating the neoplastic disease condition of choice.

The present disclosure also provides kits for producing single-dose or multi-dose administration units of antibodies and, optionally, one or more anti-cancer agents. The kit comprises a container and a label or package insert on or associated with the container. Suitable containers include, for example, bottles, vials, syringes, etc. The containers may be formed from a variety of materials such as glass or plastic and contain a pharmaceutically effective amount of the disclosed antibodies in a conjugated or unconjugated form. In other preferred embodiments, the container(s) comprise a sterile access port (for example the container may be an intravenous solution bag or a vial having a stopper pierceable by a hypodermic injection needle). Such kits will generally contain in a suitable container a pharmaceutically acceptable formulation of the antibodies and, optionally, one or more anti-cancer agents in the same or different containers. The kits may also contain other pharmaceutically acceptable formulations, either for diagnosis or combined therapy. For example, in addition to the antibody or the antigen-binding portion thereof of the disclosure such kits may contain any one or more of a range of anti-cancer agents such as chemotherapeutic or radiotherapeutic drugs; anti-angiogenic agents; anti-metastatic agents; targeted anti-cancer agents; cytotoxic agents; and/or other anti-cancer agents.

More specifically the kits may have a single container that contains the disclosed the antibody or the antigen-binding portion thereof, with or without additional components, or they may have distinct containers for each desired agent. Where combined therapeutics are provided for conjugation, a single solution may be pre-mixed, either in a molar equivalent combination, or with one component in excess of the other. Alternatively, the antibodies and any optional anti-cancer agent of the kit may be maintained separately within distinct containers prior to administration to a patient. The kits may also comprise a second/third container means for containing a sterile, pharmaceutically acceptable buffer or other diluents such as bacteriostatic water for injection (BWFI), phosphate-buffered saline (PBS), Ringer's solution and dextrose solution.

When the components of the kit are provided in one or more liquid solutions, the liquid solution is preferably an aqueous solution, with a sterile aqueous or saline solution being particularly preferred. However, the components of the kit may be provided as dried powder(s). When reagents or components are provided as a dry powder, the powder can be reconstituted by the addition of a suitable solvent. It is envisioned that the solvent may also be provided in another container.

As indicated briefly above the kits may also contain a means by which to administer the antibody or the antigen-binding portion thereof and any optional components to a patient, e.g., one or more needles, I.V. bags or syringes, or even an eye dropper, pipette, or other such like apparatus, from which the formulation may be injected or introduced into the animal or applied to a diseased area of the body. The kits of the present disclosure will also typically include a means for containing the vials, or such like, and other component in close confinement for commercial sale, such as, e.g., injection or blow-molded plastic containers into which the desired vials and other apparatus are placed and retained.

Sequence Listing Summary

Appended to the instant application is a sequence listing comprising a number of nucleic acid and amino acid sequences. The following Table A, B, C and D provide a summary of the included sequences.

The final lead anti-CD40 antibody illustrated herein is designated as "W3525-1.9.16-P5-uIgG2K" or abbreviated as "W3525" antibody. Its parental antibody "W3525-1.9.16-uIgG2K" differs from W3525 by one amino acid substitution in the light chain CDR1. The CDRs, VH and VL amino acid sequences, and nucleotide sequences encoding the variable regions are listed in the tables below.

TABLE A

CDR amino acid sequences

| | | CDR1 | CDR2 | CDR3 |
|---|---|---|---|---|
| W3525-1.9.16-uIgG2K | HCDR | SEQ ID NO: 1 GDTVSSYGIS | SEQ ID NO: 2 GSIPFFGTPNYA QKFQG | SEQ ID NO: 3 ARRGYSYGH YHYYAMDV |
| | LCDR | SEQ ID NO: 7 RSGQSLLHNN GYNYLD | SEQ ID NO: 5 LGSNRAS | SEQ ID NO: 6 MQALQTPLS |
| W3525-1.9.16-P5-uIgG2K | HCDR | SEQ ID NO: 1 GDTVSSYGIS | SEQ ID NO: 2 GSIPFFGTPNYA QKFQG | SEQ ID NO: 3 ARRGYSYGH YHYYAMDV |
| | LCDR | SEQ ID NO: 4 RSGQSLLHNN AYNYLD | SEQ ID NO: 5 LGSNRAS | SEQ ID NO: 6 MQALQTPLS |

TABLE B

Variable region amino acid sequences

| | VH | VL |
|---|---|---|
| W3525-1.9.16-uIgG2K | SEQ ID NO: 8 QVQLVQSGAEVKKPGSSVK VSCKASGDTVSSYGISWVR QAPGQGLEWMGGSIPFFGT PNYAQKFQGRVTFTADEST STAYMELSSLRSEDTAVYY CARARRGYSYGHYHYYAMD VWGQGTTVTVAS | SEQ ID NO: 10 DTVMTQSPLSLPVTPGEPASI SCRSGQSLLHNNGYNYLDWYL QKPGQSPQLLIYLGSNRASGV PDRFSGSGSGTDFTLKISRVE AEDVGVYYCMQALQTPLSFGG GTKVEIK |
| W3525-1.9.16-P5-uIgG2K | SEQ ID NO: 8 QVQLVQSGAEVKKPGSSVK VSCKASGDTVSSYGISWVR QAPGQGLEWMGGSIPFFGT PNYAQKFQGRVTFTADEST STAYMELSSLRSEDTAVYY CARARRGYSYGHYHYYAMD VWGQGTTVTVAS | SEQ ID NO: 9 DTVMTQSPLSLPVTPGEPASI SCRSGQSLLHNNAYNYLDWYL QKPGQSPQLLIYLGSNRASGV PDRFSGSGSGTDFTLKISRVE AEDVGVYYCMQALQTPLSFGG GTKVEIK |

TABLE C

Variable region nucleotide sequences

| | VHnu | VLnu |
|---|---|---|
| W3525-1.9.16-uIgG2K | SEQ ID NO: 11 CAGGTGCAGCTGGTGCAG TCTGGGGCTGAGGTGAAG AAGCCTGGGTCCTCGGTG AAGGTCTCCTGCAAGGCT TCTGGAGACACCGTCAGC AGCTATGGTATCAGCTGG GTGCGACAGGCCCCTGGA CAAGGGCTTGAGTGGATG GGAGGGAGCATCCCTTTC TTTGGTACACCAAACTAC GCACAGAAGTTCCAGGGC AGAGTCACGTTTACCGCG GACGAATCCACGAGCACA GCCTACATGGAGCTGAGC AGCCTGAGATCTGAGGAC ACGGCCGTGTATTACTGT GCGAGAGCGAGACGTGGA TACAGCTATGGTCACTAC CACTACTACGCTATGGAC GTCTGGGGCCAAGGGACC ACGGTCACCGTCGCCTCA | SEQ ID NO: 13 GATACTGTGATGACTCAGTCTC CACTCTCCCTGCCCGTCACCCC TGGAGAGCCGGCCTCCATCTCC TGCAGGTCTGGTCAGAGCCTCC TGCATAATAATGGATACAACTA TTTGGATTGGTACCTGCAGAAG CCAGGGCAGTCTCCACAGCTCC TGATCTATTTGGGTTCTAATCG GGCCTCCGGGGTCCCTGACAGG TTCAGTGGCAGTGGATCAGGCA CAGATTTTACACTGAAAATCAG CAGAGTGGAGGCTGAGGATGTT GGGGTTTATTACTGCATGCAAG CTCTACAAACTCCTCTCAGTTT CGGCGGAGGGACCAAGGTGGAG ATCAAA |
| W3525-1.9.16-P5-uIgG2K | SEQ ID NO: 11 CAGGTGCAGCTGGTGCAG TCTGGGGCTGAGGTGAAG AAGCCTGGGTCCTCGGTG AAGGTCTCCTGCAAGGCT TCTGGAGACACCGTCAGC AGCTATGGTATCAGCTGG GTGCGACAGGCCCCTGGA CAAGGGCTTGAGTGGATG GGAGGGAGCATCCCTTTC TTTGGTACACCAAACTAC GCACAGAAGTTCCAGGGC AGAGTCACGTTTACCGCG GACGAATCCACGAGCACA GCCTACATGGAGCTGAGC AGCCTGAGATCTGAGGAC ACGGCCGTGTATTACTGT GCGAGAGCGAGACGTGGA TACAGCTATGGTCACTAC CACTACTACGCTATGGAC GTCTGGGGCCAAGGGACC ACGGTCACCGTCGCCTCA | SEQ ID NO: 12 GATACTGTGATGACTCAGTCTC CACTCTCCCTGCCCGTCACCCC TGGAGAGCCGGCCTCCATCTCC TGCAGGTCTGGTCAGAGCCTCC TGCATAATAATGCGTACAACTA TTTGGATTGGTACCTGCAGAAG CCAGGGCAGTCTCCACAGCTCC TGATCTATTTGGGTTCTAATCG GGCCTCCGGGGTCCCTGACAGG TTCAGTGGCAGTGGATCAGGCA CAGATTTTACACTGAAAATCAG CAGAGTGGAGGCTGAGGATGTT GGGGTTTATTACTGCATGCAAG CTCTACAAACTCCTCTCAGTTT CGGCGGAGGGACCAAGGTGGAG ATCAAA |

TABLE D

Full length sequences

| | SEQ ID NO: 14 | SEQ ID NO: 15 |
|---|---|---|
| W3525-1.9.16-P5-uIgG2K | Heavy chain, full sequence | Light chain, full sequence |

EXAMPLES

The present disclosure, thus generally described, will be understood more readily by reference to the following Examples, which are provided by way of illustration and are not intended to be limiting of the present disclosure. The Examples are not intended to represent that the experiments below are all or the only experiments performed.

Example 1

Preparation of Materials, Benchmark Antibodies and Cell Lines 1.1 Preparation of Materials Information on the commercially available materials used in the examples is provided in Table 1.

TABLE 1

| Materials | Vendor | Catalog Number (Cat.) |
|---|---|---|
| Anti-Human CD40 PE | eBioscience | 12-0409-42 |
| Anti-Mouse CD40 PE | eBioscience | 12-0401-82 |
| Alexa647 goat anti-human IgG | JacksonImmunoResearch | 109-605-097 |
| R-PE goat anti-human IgG | JacksonImmunoResearch | 109-115-098 |
| BSA | Bovogen | BSAS1.0 |
| PE goat anti-mouse IgG | Abcam | ab98742 |
| Mouse IgG1 kappa isotype control, PE | eBioscience | 12-4714-82 |
| Human GITR protein (His tag, ECD) | SinoBiological | 13643-H08H |
| HRP goat anti-human IgG | Bethyl | A80-304P |
| CD40 protein, canine, recombinant (His tag) | SinoBiological | 70105-D08H |
| CD40 protein, rat, recombinant (His tag) | SinoBiological | 80151-R08H |
| Series sensor chip CM5 | GE | 29-1496-03 |
| Amine coupling kit | GE | BR100050 |
| 10× HBS-EP+ | GE | BR100669 |
| Goat anti-human IgG | JacksonImmunoResearch | 109-005-098 |
| GLM chip | Bio-Rad | 176-5012 |
| ProteOn amine coupling kit | Bio-Rad | 176-2410 |
| Nano-Glo luciferase assay system | Promega | N1150 |
| EasySep ™ human CD19 positive selection kit II | StemCell | 17854 |
| CellTiter-Glo luminescent cell viability assay system | Promega | G7573 |
| CD14 microbeads, human | Miltenyi Biotec | 130-050-201 |
| GM-CSF | R&D | 215-GM |
| IL-4 | R&D | 204-IL |
| Human IL-12 (p40) ELISA set kit | BD | 555171 |
| APC mouse anti-human CD54 | BD | 559771 |
| PE mouse anti-human CD80 | BD | 557227 |
| PE mouse anti-human CD83 | BD | 556855 |
| FITC mouse anti-human CD86 | BD | 555657 |
| Streptavidin-HRP | Invitrogen | SNN1004 |
| CD19 microbeads, human | Miltenyi Biotec | 130-050-301 |
| One-Glo luciferase assay system | Promega | E6130 |
| Human Th1/Th2/Th17 cytokine kit | BD | 560484 |
| Ficoll-Paque | StemCell | 07861 |
| LPS | Sigma | L5418 |
| SuperScript ™ III First-Strand Synthesis SuperMix Kit | Invitrogen | 18080400 |
| SYPRO ™ orange protein gel stain | Invitrogen | S6651 |
| QuikChange lightning multi site-directed mutagenesis kits | Agilent | 210514 |
| His tag antibody [HRP], mAb, mouse | Genscrip | A00612 |
| CHO-K1 | NTCC | GNHa 7 |
| Raji | ATCC | CCL-86 |
| A431 | ATCC | CRL-1555 |
| Ramos | ATCC | CRL-1923 |
| U937 | ATCC | CRL-1593.2 |
| Jurkat | ATCC | TIB-152 |

The information of the material code is indicated in Table 2 below.

TABLE 2

| Materials code | |
|---|---|
| Code | Information |
| W3525-1.9.16-P5-uIgG2K | Final lead antibody, may be abbreviated as "W3525" or "W3525 antibody" |
| WBP352-BMK3.uIgG1K | Benchmark antibody 3 or abbreviated as "BMK3" |
| WBP352-BMK4.hIgG2K | Benchmark antibody 4 or abbreviated as "BMK4" |
| WBP352-BMK5.hIgG1K | Benchmark antibody 5 or abbreviated as "BMK5" |

TABLE 2-continued

| Materials code | |
|---|---|
| Code | Information |
| WBP352-BMK7-uIgG2K | Benchmark antibody 7 or abbreviated as "BMK7" |
| W352-hPro1.ECD.hFc | Human CD40 extracellular domain, hFc tag |
| W352-mPro1.ECD.hFc | Mouse CD40 extracellular domain, hFc tag |
| W352-hPro1.ECD.His | Human CD40 extracellular domain, His tag |
| W352-mPro1.ECD.His | Mouse CD40 extracellular domain, His tag |
| W352-cynoPro1.ECD.His | Cynomolgus monkey CD40 extracellular domain, His tag |
| W352-hpro1L1.ECD.mFc | Human CD40L extracellular domain, mFc tag |
| W352-Ramos.NFkBRE.luc | Ramos cells transfected with NFκB-luciferase reporter gene |
| W352-U937.hPro1.NFkBRE.luc | U937 cells over-expressing human CD40 and NFκB-luciferase reporter gene |
| Jurkat-NFAT-CD16.A5 | Jurkat cells over-expressing human FcγRIIIa(V158) and NFAT-luciferase reporter gene |

1.2 Production of Antigens

Antigens W352-hPro1.ECD.hFc (NP_001241.1, 21-193), W352-mPro1.ECD.hFc (NP_035741.2, 20-193), W352-hPro1.ECD.His (NP_001241.1, 21-193), W352-mPro1.ECD.His (NP_035741.2, 20-193), W352-cynoPro1.ECD.Mis (XP_005569274.1, 21-193), W352-hpro1L1.ECD.mFc (NP_000065.1, 47-261) were expressed and produced in human Expi-293F cells. The antigen proteins were purified and stored at −80° C.

1.3 Production of Benchmark Antibodies

Anti-human CD40 antibodies BMK3, BMK4, BMK5 and BMK7 were used as benchmark antibodies in the following studies. Their variable domains were synthesized according to the disclosed sequences in respective patent, the information of which is summarized in Table 3. BMK4 and BMK7 were constructed by fusing the variable domains with human IgG2 (kappa light chain) constant domain, while BMK3 and BMK5 were constructed by fusing the variable domains with human IgG1 (kappa light chain) constant domain. Human IgG1/IgG2 antibodies were used as isotype control antibodies. All above antibodies were stored at −80° C.

TABLE 3

| Reference antibody information | | | |
|---|---|---|---|
| Antibody Code | Company | Patent NO. | Molecular Name |
| WBP352-BMK3.uIgG1K | Novartis | US20140205602 | CHIR-12.12 |
| WBP352-BMK4.hIgG2K | Pfizer | US20160152713 | 21.4.1/CP-870,893 |
| WBP352-BMK5.hIgG1K | Apexigen | US20160208007 | APX005 |
| WBP352-BMK7-uIgG2K | CellDex | WO2017184619 | 3C3/CDX-1140 |

1.4 Cell Pool/Line Generation

Human CD40-expressing cell line W352-CHOK1.hPro1.A7 was generated using CHO-K1 cells transfected with full-length human CD40 (NM_001250.5, NP_001241.1).

Mouse CD40-expressing cell line W352-CHOK1.mPro1.B3 was generated using CHO-K1 cells transfected with full-length mouse CD40 (NP_035741.2).

The reporter cell pool W352-Ramos.NFkBRE.luc was transfected with a vector containing five copies of NF-κB response element that drives transcription of a destabilized form of Nanoluc luciferase fusion protein (JQ513377.1).

The reporter cell pool W352-U937.hPro1.NFkBRE.luc was co-transfected with two vectors, one containing full-length human CD40 (NM_001250.5, NP_001241.1), and the other containing five copies of NF-κB response element driving transcription of a destabilized form of Nanoluc luciferase fusion protein (JQ513377.1).

The reporter cell line Jurkat-NFAT-CD16.A5 was co-transfected with two vectors, one containing full-length human FcγRIIIa (NM_000569.7, NP_000560.6), V158 variant, and the other containing an NFAT response element driving expression of a firefly luciferase (DQ904462).

Example 2

Antibody Hybridoma Generation, Screening and Optimization 2.1 Immunization

OMNIRAT™ is a transgenic rat developed by Open Monoclonal Technology Company, which carries a chimeric human/rat IgH locus (comprising 22 human $V_H$S, all human D and $J_H$ segments in natural configuration linked to the rat CH locus) together with fully human IgL loci (12 Vκs linked to Jκ-Cκ and 16 Vλs linked to Jλ-Cλ)[2-3]. The endogenous Ig loci were silenced using designer zinc finger nucleases. OMNIRAT™ rat could produce antibodies with human idiotypes as efficiently as wild-type animals produce rat antibodies.

Two OMNIRAT™ rats, 6~8 weeks old, a male and a female, were immunized with 40 μg of W352-hPro1.ECD.hFc and W352-mPro1.ECD.hFc together or alternately. The immunization was repeated roughly every one or two weeks for a total of 182 days.

2.2 Serum Titer Detection

Anti-human/mouse CD40 antibody titers in serum samples were determined by ELISA. Microplates were coated with W352-hPro1.ECD.His or W352-mPro1.ECD.His at 0.5 μg/mL in 100 μL of coating buffer (0.02 M $Na_2CO_3$ and 0.18 M $NaHCO_3$, pH 9.2) per well and incubated at 4° C. overnight. On the day of assay, diluted rat serum samples (first 1:100, then 3-fold dilution with 1×PBS/2% BSA) and negative control were added into the plates post 1-hour block with 1×PBS/2% BSA, and then the plates were incubated at ambient temperature for 2 h. After washing with 1×PBST (PBS containing 0.05% Tween-20) for 3 times, HRP-labeled goat anti-rat IgG Fc was added and incubated at ambient temperature for 1 hour. After removing of the unbound substance, TMB (3,3',5,5'-Tetramethylbenzidine) substrate was added and the reaction was stopped by 2M HCl. Absorbance at 450 nm was detected by a microplate spectrophotometer.

The serum titers of the immunized OMT rats are shown in Table 4. The Rat #1 was selected for a final antigen boost after the 2$^{nd}$ bleed and were euthanized, the lymph nodes of which were collected and used for fusion.

TABLE 4

Serum titer of anti-CD40 antibodies

| Animal ID # | Antigen | Titer information: Pre-bleed | 1$^{st}$ bleed | 2$^{nd}$ bleed | 3$^{rd}$ bleed | 4$^{th}$ bleed |
|---|---|---|---|---|---|---|
| 1 | W352- | <100 | 656100 | 218700 | / | / |
| 2 | hPro1.ECD.His | <100 | 218700 | 218700 | 218700 | 218700 |
| 1 | W352- | <100 | 72900 | 656100 | / | / |
| 2 | mPro1.ECD.His | <100 | 24300 | 72900 | 72900 | 218700 |

2.3 Hybridoma Generation

Lymph nodes were collected from OMT rat under sterile condition and dissociated into single cell suspension. The isolated cells were then mixed with myeloma cell SP2/0 at a ratio of 1:1.2. Electro cell fusion was performed using BTX 2001 Electro cell manipulator according to manufacturer's instruction. After fusion, cell suspension from the fusion chamber was immediately transferred into a sterile tube containing more medium and incubated for at least 24 hours in a 37° C., 5% $CO_2$ incubator. The cell suspension was mixed and transferred into 96-well plates (1x10$^4$ cells/well). The 96-well plates were cultured at 37° C., 5% $CO_2$, and were monitored periodically. When the clones reached about 80% confluence in a well, 100 μL of supernatant were transferred from the tissue culture plates to 96-well assay plates for antibody screening.

2.4 Antibody Screening and Subcloning

The process of high-throughput screening included primary screening by ELISA (Screening for human CD40 binder), confirmation screening by FACS/ELISA (Screening for human and mouse CD40 binder by FACS, Screening for monkey CD40 binder by ELISA, Screening for antibodies blocking human CD40/CD40L interaction) and functional screening by NFκB reporter gene assay (Screening for antibodies that can activate CD40 pathway by RGA). Based on the binding, competition and functional activity, total 30 hybridoma lines were identified for sub-cloning.

Each line of hybridoma cell at logarithmic phase was diluted to 150-200 cells per 1.5 mL semi-solid HAT media. The cell suspensions were mixed gently on vortex oscillator and then seeded in a well of 6-well plate. When the cell clusters grew up, each visible single colony was picked and seeded into 96-well plates with DMEM medium supplemented with 10% fatal bovine serum. After 2-3 days' culture, the supernatant of single clones was collected for purification.

After sub-cloning, total 500 single clones were obtained, all of which went forward for the next round of high-throughput screening. Twenty-six positive clones were selected for purification and sequencing, and further characterization.

2.5 Antibody Optimization 2.5.1 IgG Conversion

After sequence analysis and functional screening, the candidates were selected for fully human antibody construction.

The DNA sequences of the variable domain of these candidates were synthesized and cloned into pCI vector containing human IgG2 Fc. After sequence confirming, the expression vectors containing whole IgG of fully human antibodies were used for transient transfection for antibodies production.

2.5.2 PTM Removal

The amino acid "NG" in CDR1 of candidate W3525-1.9.16-uIgG2K light chain was identified as a high-risk deamidation site, so antisense mutagenic nucleotides were designed to introduce some mutations into "W3525-1.9.16-uIgG2K" light chain.

Based on the comparison of binding affinity and agonistic activity, W3525-1.9.16-P5-uIgG2K (referred to as W3525 antibody) was selected as the final lead antibody from the variants.

Example 3

In Vitro Characterization of the W3525 Antibody 3.1 Human CD40 Binding Assay (FACS)

W352-CHOK1.hPro1.A7 (1x10$^5$ cells/well), Raji (1x10$^5$ cells/well) or A431 (5x10$^4$ cells/well) cells were incubated with various concentrations of W3525 antibody (3-fold serially diluted from 100 nM to 0.0051 nM, or 5-fold serially diluted from 100 nM to 0.00128 nM) at 4° C. for 1 hour. After washing with 1×PBS/1% BSA, the secondary antibody, Alex647-labeled goat anti-human IgG (1:250) or R-PE-labeled goat anti-human IgG (1:150) was added and incubated with cells at 4° C. in dark for 1 hour. Anti-human CD40 antibodies BMK4 and BMK5 were used as positive controls. Human IgG1 and IgG2 isotype antibodies were used as isotype controls. The cells were then washed and re-suspended in 1×PBS/1% BSA. MFI of the cells was measured by a flow cytometer and analyzed by FlowJo. GraphPad Prism was used to plot the log of antibody concentration (x-axis) versus MFI (y-axis). The EC50 values were determined using four-parameter dose-response curve model.

Figure 2:
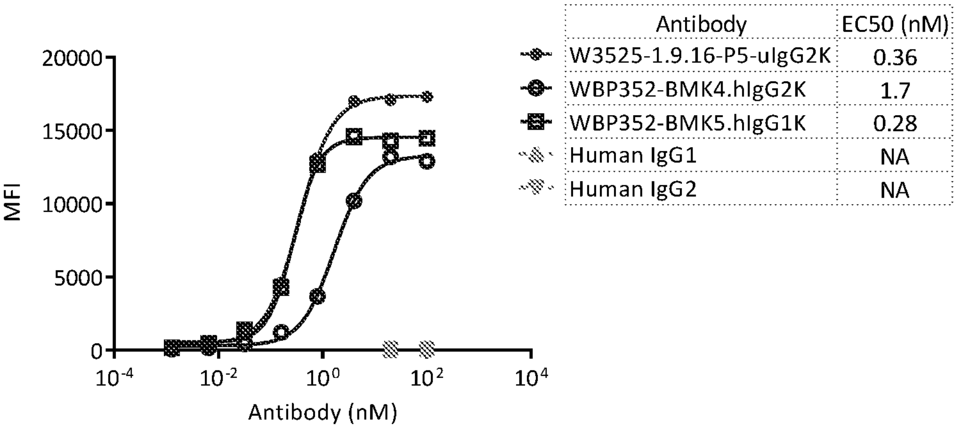
Figure 3:
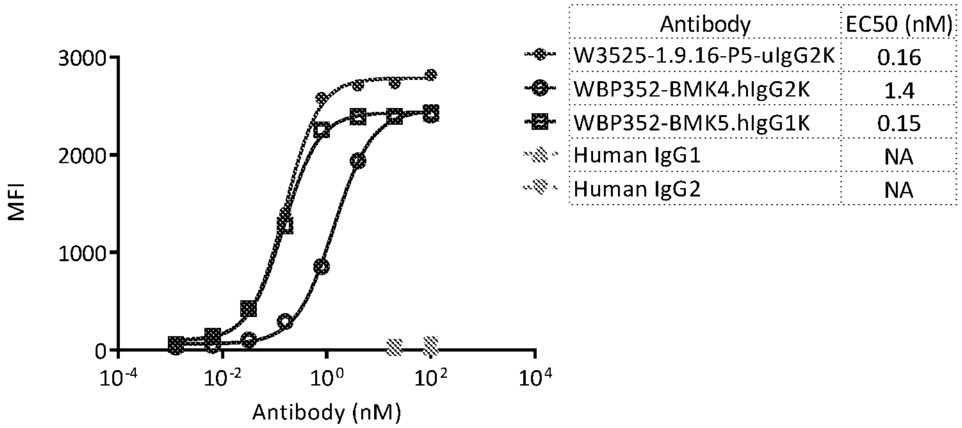

The binding result of W3525 on W352-CHOK1.hPro1.A7, Raji and A431 cells are shown in FIGS. 1, 2 and 3, respectively. W3525 can strongly bind to cell surface human CD40 with an EC50 of 1.1 nM; can strongly bind to Raji cells with an EC50 of 0.36 nM; can strongly bind to A431 cells with an EC50 of 0.16 nM, comparable to or better than the reference antibodies.

3.2 Cynomolgus Monkey CD40 Binding Assay (FACS)

Cynomolgus monkey CD40 transiently transfected 293F cells (2x10$^5$ cells/well) were incubated with various concentrations of W3525 (3-fold serially diluted from 200 nM to 0.0102 nM) at 4° C. for 1 hour. After washing with 1×PBS/1% BSA, a secondary antibody, R-PE-labeled goat anti-human IgG (1:150) was added and incubated with cells at 4° C. in dark for 1 hour. The cells were washed and suspended and the MFI and EC50 values were determined as described above.

Figure 4:
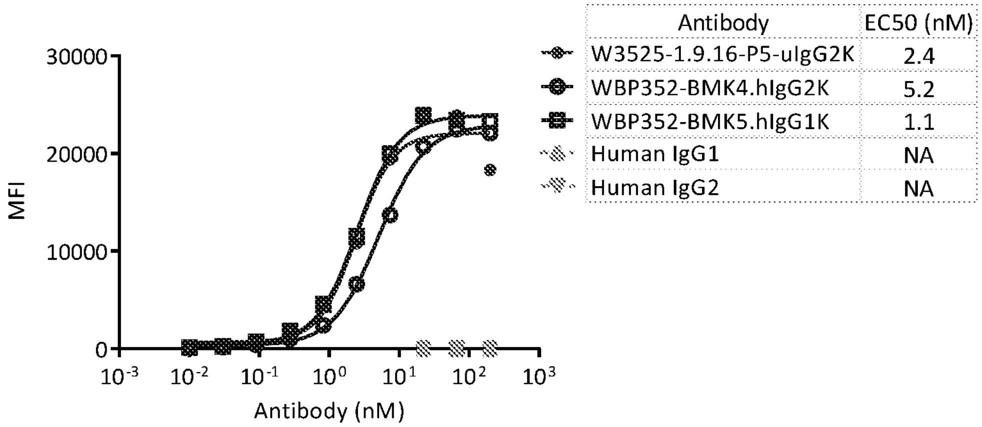
FIG. 4 illustrates the binding result of W3525-1.9.16-P5-uIgG2K to cell surface cynomolgus monkey CD40 by FACS.

The binding result of W3525 to cell surface cynomolgus monkey CD40 is shown in FIG. 4. W3525 showed strong binding to cell surface cynomolgus monkey CD40 with an EC50 of 2.4 nM, comparable to the reference antibodies.

3.3 Ligand Binding Competition Assay (FACS)

W352-CHOK1.hPro1.A7 cells were plated in a 96-well plate at a density of $1\times10^5$ cells/well. A constant concentration of W352-hPro1L1.ECD.mFc (5 μg/mL) diluted in 1×PBS/1% BSA was added to the cells, followed by serially diluted antibodies (3-fold serially diluted from 60 nM to 0.0274 nM in 1×PBS/1% BSA), and mixed well. The plate was incubated at 4° C. for 1 hour.

Figure 5:
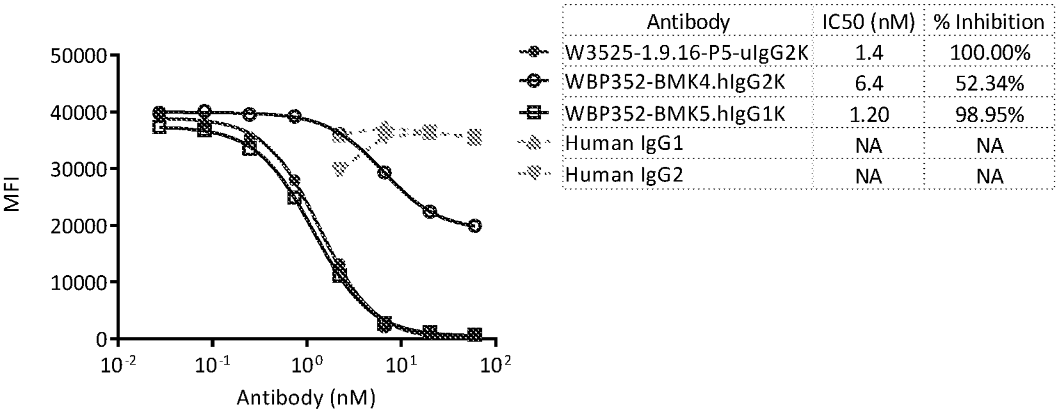
FIG. 5 illustrates the result of antibodies competing with CD40L for CD40 binding by FACS.

The human CD40/CD40L competition result is shown in FIG. 5. W3525 can effectively compete with human CD40L for binding to CD40 with an IC50 of 1.4 nM and 100% inhibition rate, while BMK4 can only partially compete with CD40L for CD40 binding. Note: % inhibition=($MFI_{top}$−$MFI_{bottom}$)/$MFI_{top}$×100%.

3.4 CD40 Homologous Protein Binding Assay (ELISA)

Plate was pre-coated with 1 μg/mL of recombinant human CD40, OX40, 4-1BB, GITR or BCMA extracellular domain in 100 μL coating buffer (0.02 M $Na_2CO_3$ and 0.18 M $NaHCO_3$, pH9.2) per well at 4° C. overnight. Next day, the plate was washed with 1×PBST for one time. After 1-hour blocking using 200 μL of 1×PBS/2% BSA, the plate was washed using 1×PBST for 3 times. W3525 was added to the plate at a concentration of 66.7 nM and incubated at ambient temperature for 1 hour. Anti-CD40 antibodies BMK4 and BMK5, anti-OX40 antibody MEDI0562, anti-4-1BB antibody BMS-663513, anti-GITR antibody INCAGN01876 and anti-BCMA antibody EM801 were used as positive controls, respectively. Human IgG2 isotype antibody was used as isotype control. After incubation, the plate was washed using 1×PBST for 3 times. HRP-labeled goat anti-human IgG antibody diluted in 1×PBS/2% BSA at a ratio of 1:5000 was added and incubated for 1 hour. After washing with 1×PBST for 6 times, the color was developed by dispensing 100 μL of TMB substrate, and then reaction was stopped by adding 100 μL of 2M HCl. Absorbance was read at 450 nm and 540 nm using a microplate spectrophotometer. GraphPad Prism was used to plot the antibody concentration (x-axis) versus absorbance (y-axis). All samples were tested in duplicate.

Figure 6:
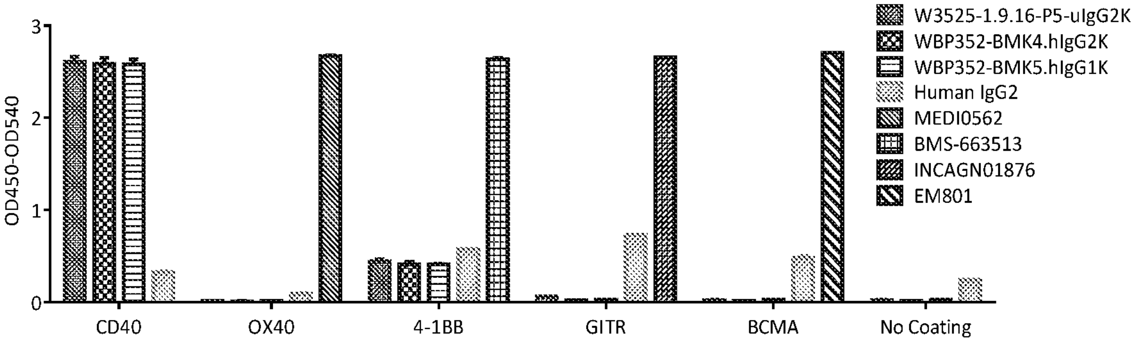
FIG. 6 illustrates the binding result of W3525-1.9.16-P5-uIgG2K to members of TNFR superfamily that share homology with CD40.

The binding result of W3525 to members of TNFR superfamily that share homology with CD40 is shown in FIG. 6. The W3525 antibody can specifically bind to human CD40, without cross-reactivity to human OX40, 4-1BB, GITR and BCMA.

3.5 Cross-Species Protein Binding (ELISA)

Plate was pre-coated with 1 μg/mL of recombinant human, cynomolgus monkey, mouse, canine or rat CD40 extracellular domain in 100 μL coating buffer per well at 4° C. overnight. Then the ELISA procedure was performed as described above. Anti-human CD40 antibodies BMK4 and BMK5 were used as positive controls. Human IgG1 and IgG2 isotype antibodies were used as isotype controls.

Figure 7:
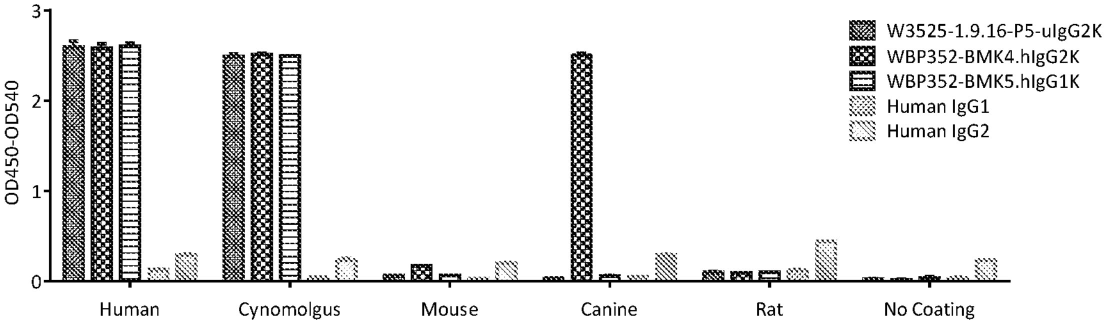
FIG. 7 illustrates the comparative binding result of W3525-1.9.16-P5-uIgG2K to human, cynomolgus monkey, mouse, rat and canine CD40 protein by ELISA.

The comparative binding result of W3525 to human, cynomolgus monkey, mouse, rat and canine CD40 protein is shown in FIG. 7. W3525 shows cross-reactivity to human and cynomolgus monkey CD40, but no cross-reactivity to mouse, rat and canine CD40, while BMK4 shows cross-reactivity to canine CD40.

3.6 Affinity to Human CD40 (SPR)

Surface plasmon resonance (SPR) was used to perform full binding kinetics analysis in order to determine the binding affinity of W3525 to recombinant CD40 extracellular domain in a quantitative manner. SPR allows real-time, label-free detection of bio-molecular interactions. SPR occurs when polarized light strikes an electrically conducting surface at the interface between two media. This generates electron charge density waves called plasmon, reducing the intensity of reflected light at a specific angle known as the resonance angle, in proportion to the mass on a sensor surface.

The affinity of W3525 to human CD40 was determined using Biacore 8K. The activator was prepared by mixing 400 mM EDC and 100 mM NHS immediately prior to injection. The CM5 sensor chip was activated for 420s with the activator at a flow rate of 10 μL/min. Goat anti-human Fc IgG (30 μg/mL in 10 mM NaAc, pH 4.5) was then injected to the channels for 420s at a flow rate of 10 μL/min. The chip was deactivated by 1 M ethanolamine-HCl at a flow rate of 10 μL/min for 420s. After immobilization, the antibody W3525 was diluted to 66.7 nM in running buffer (1×HBS-EP+) and was captured onto the channel Fc4 at a flow rate of 10 μL/min for 30s. Seven concentrations (0, 1.5625, 3.125, 6.25, 12.5, 25 and 50 nM) of analyte W352-hPro1.ECD.His were injected orderly to the channels at a flow rate of 30 μL/min for an association phase of 90s, followed by 300s dissociation. Glycine solution (10 mM, pH 1.5) as regeneration buffer was injected following dissociation phase to regenerate the chip.

The affinity of BMK4 and BMK5 to human CD40 was determined using ProteOn XPR36. The activator was prepared by mixing 40 mM EDC and 100 mM sulfo-NHS immediately prior to injection. The GLM sensor chip was activated for 300s with the activator at a flow rate of 30 μL/min. Goat anti-human Fc IgG (30 μg/mL in 10 mM NaAc, pH 4.5) was then injected to the channels for 300s at a flow rate of 30 μL/min. The chip was deactivated by 1 M ethanolamine-HCl at a flow rate of 30 μL/min for 300s. The antibody BMK5 was diluted to 13.34 nM in running buffer (1×HBS-EP+) and was injected to the L4 channel at a flow rate of 30 μL/min for 100s. The chip was rotated 900 and washed with running buffer until the baseline was stable. Six concentrations (10, 5, 2.5, 1.25, 0.625 and 0 nM) of analyte W352-hPro1.ECD.His were injected orderly to the A1-A6 channels at a flow rate of 100 μL/min for an association phase of 120s, followed by 240s dissociation. Glycine solution (10 mM, pH 1.5) as regeneration buffer was injected following dissociation phase to regenerate the chip. After regeneration, the antibody BMK4 was diluted to 13.34 nM in running buffer (1×HBS-EP+) and was injected to the L3 channel at a flow rate of 30 μL/min for 80s. The chip was rotated 90° and washed with running buffer until the baseline was stable. Six concentrations (40, 20, 10, 5, 2.5 and 0 nM) of analyte W352-hPro1.ECD.His were injected orderly to the A1-A6 channels at a flow rate of 100 μL/min for an association phase of 240s, followed by 600s dissociation. After each cycle, glycine solution (10 mM, pH 1.5) as regeneration buffer was injected to regenerate the chip.

The sensorgrams for reference channel and buffer channel were subtracted from the test sensorgrams. The experimental data was fitted based on the 1:1 binding model.

Molecular weight of 29 kDa was used to calculate the molar concentration of W352-hPro1.ECD.His. The kinetic affinity of W3525 to W352-hPro1.ECD.His is shown in Table 5, and the affinity constant is 7.12 nM.

TABLE 5

| Affinity to human CD40 free protein | | | |
| --- | --- | --- | --- |
| Antibody | ka (1/Ms) | kd (1/s) | KD (nM) |
| BMK4 | 2.30E+05 | 1.11E−03 | 4.83 |
| BMK5 | 1.12E+06 | 5.09E−03 | 4.56 |
| W3525 | 5.69E+05 | 4.05E−03 | 7.12 |

3.7 Affinity to Monkey CD40 (SPR)

The affinity of BMK4 and BMK5 to cynomolgus monkey CD40 was determined using Biacore 8K. The process of immobilization was the same as above. The antibodies BMK4 and BMK5 were diluted to 33.35 nM in running buffer (1×HBS-EP+) and was respectively captured onto Fc2 of channel 6 and 7 at a flow rate of 10 μL/min for 30s. Seven concentrations (0, 1.563, 3.125, 6.25, 12.5, 25 and 50 nM) of analyte W352-cynoPro1.ECD.His were injected orderly to Fc1 and Fc2 of the channels at a flow rate of 30 μL/min for an association phase of 240s, followed by 600s dissociation. Glycine solution (10 mM, pH 1.5) as regeneration buffer was injected following dissociation phase to regenerate the chip.

The affinity of W3525 to cynomolgus monkey CD40 was determined using Biacore T200. The process of immobilization was the same as that of Biacore 8K. The antibody W3525 was diluted to 33.35 nM in running buffer (1×HBS-EP+) and was captured onto Fc2 at a flow rate of 10 μL/min for 60s. Seven concentrations (0, 1.56, 3.13, 6.25, 12.5, 25 and 50 nM) of analyte W352-cynoPro1.ECD.His were injected orderly to Fc1 and Fc2 at a flow rate of 30 μL/min for an association phase of 240s, followed by 300s dissociation. After each cycle, glycine solution (10 mM, pH 1.5) as regeneration buffer was injected to regenerate the chip.

Molecular weight of 29 kDa was used to calculate the molar concentration of W352-cPro1.ECD.His. The kinetic affinity of W3525 to W352-cPro1.ECD.His is shown in Table 6, and the affinity constant is 8.47 nM.

TABLE 6

Affinity to cynomolgus monkey CD40 free protein

| Antibody | ka (1/Ms) | kd (1/s) | KD (nM) |
|---|---|---|---|
| BMK4 | 1.55E+05 | 1.07E−03 | 6.94 |
| BMK5 | 5.68E+05 | 8.82E−03 | 15.5 |
| W3525 | 4.44E+05 | 3.77E−03 | 8.47 |

3.8 NFκB Reporter Assays

Two NFκB luciferase reporter cell lines W352-Ramos.NFκBRE.luc and W352-U937.hPro1.NFκBRE.luc were developed to assess the agonistic activity of W3525 on CD40 pathway. The cells were plated in a 96-well plate at $4\times10^4$ cells/well in a volume of 50 μL. Various concentrations of W3525 (10-fold serially diluted from 100 nM to 0.00001 nM) were subsequently added to the cells in a volume of 50 μL. Anti-human CD40 antibodies BMK4 and BMK5 were used as positive controls. Human IgG1 and IgG2 isotype antibodies were used as isotype controls. The plates were incubated at 37° C., 5% $CO_2$ for 5-6 hours. Reconstituted luciferase substrate was added to each well (50 μL/well) and mixed well. The luciferase intensity was read using a microplate spectrophotometer (Envision). GraphPad Prism was used to plot the log of antibody concentration (x-axis) versus fold change of luciferase intensity (y-axis). The EC50 values were determined using four-parameter dose-response curve model. The experiment was performed three times and all the samples were tested in duplicate.

Figure 8:
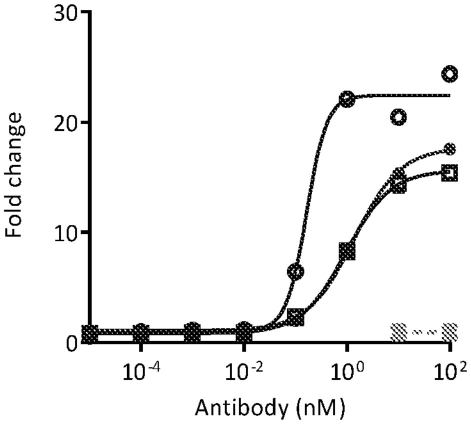
FIGS. 8-9 illustrate the result of NFκB reporter assay based on Ramos cells (FIG. 8) and U937 cells (FIG. 9).
Figure 9:
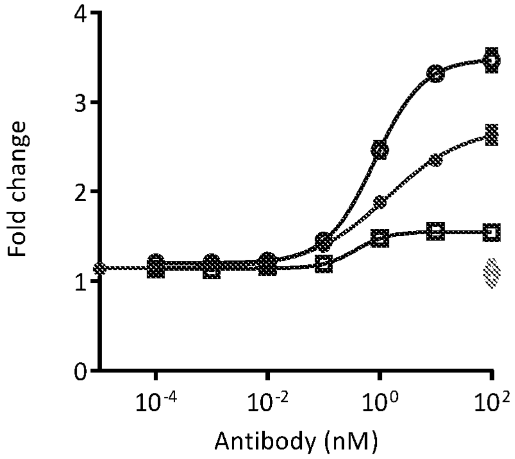

To directly demonstrate CD40 activation, two luciferase reporter cell lines (one is based on B lymphoma cell line Raji, and the other is monocytic leukemia cell line U937) were used to quantify the in vitro potency of W3525, and the data is shown in FIG. 8 and FIG. 9, and the potency data is summarized in Table 7. W3525 can induce a concentration-dependent activation of NFκB, and is demonstrated to be at a more moderate magnitude than BMK4.

TABLE 7

Potency of antibodies in NFκB reporter assay

| | W352-Ramos.NFκBRE.luc | | | W352-U937.hPro1.NFκBRE.luc | | |
|---|---|---|---|---|---|---|
| Antibody | $EC_{20}$ (nM) | $EC_{50}$ (nM) | $EC_{90}$ (nM) | $EC_{20}$ (nM) | $EC_{50}$ (nM) | $EC_{90}$ (nM) |
| W3525 | 0.32 | 1.4 | 13 | 0.15 | 1.3 | 45 |
| BMK4 | 0.087 | 0.16 | 0.45 | 0.21 | 0.81 | 7.2 |
| BMK5 | 0.24 | 0.96 | 8.5 | 0.15 | 0.37 | 1.6 |

3.9 In Vitro B Cell Proliferation Assay

Human B cells were isolated from human peripheral blood mononuclear cells (PBMCs) by magnetic selection using EasySep™ Human CD19 Positive Selection Kit II according to the manufacturer's protocol. Freshly isolated human B cells were added to each well at a density of $6\times10^4$ cells/well in a volume of 100 μL. Various concentrations of antibodies (10-fold serially diluted from 100 nM to 0.001 nM) were subsequently added to the wells in a volume of 100 μL. Anti-human CD40 antibodies BMK4 and BMK5 were used as positive controls. Human IgG1 and IgG2 isotype antibodies were used as isotype controls. The plates were incubated at 37° C., 5% $CO_2$ for 5 days and then the B cell proliferation level was determined by CellTiter-Glo according to the manufacturer's instruction. The luciferase intensity was read using a microplate spectrophotometer (M5e). GraphPad Prism was used to plot the log of antibody concentration (x-axis) versus relative light unit (y-axis). The EC50 values were determined using four-parameter dose-response curve model. The experiment was performed twice and all samples were tested in triplicate.

Figure 10:
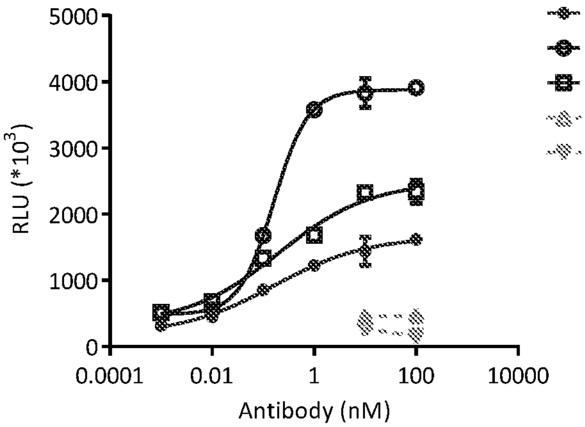
FIG. 10 illustrates the result of B cell proliferation stimulated by W3525-1.9.16-P5-uIgG2K in in vitro B cell proliferation assay.

CD40-agonistic antibodies can substitute for CD40L on activated T cells to boost immunity. CD40-activated B cells enter a proliferation state which in turn enhances the T-cell response. The result of B cell proliferation stimulated by W3525 is shown in FIG. 10, and the potency data is summarized in Table 8. W3525 can effectively enhance B cell proliferation in a dose-dependent manner, and the effect is more moderate than that of BMK4.

TABLE 8

Potency of antibodies in B cell proliferation assay

| | B Cell proliferation | | |
|---|---|---|---|
| Antibody | $EC_{20}$ (nM) | $EC_{50}$ (nM) | $EC_{90}$ (nM) |
| W3525 | 0.0089 | 0.16 | 16 |
| BMK4 | 0.0055 | 0.16 | 0.89 |
| BMK5 | 0.012 | 0.20 | 19 |

3.10 In Vitro DC Activation Assay

Human monocytes were isolated from human PBMCs by magnetic selection using human CD14 MicroBeads according to the manufacture's protocol. Freshly isolated monocytes were adjusted to $2\times10^6$ cells/mL in complete RPMI-1640 medium supplemented with recombinant human GM-CSF at 800 U/mL and IL-4 at 50 ng/mL. The cells were cultured for 4 or 5 days to induce into dendritic cells. The dendritic cells were plated in 96-well plates at a density of $1\times10^5$ cells/well in a volume of 100 μL. Various concentrations of antibodies (3-fold serially diluted from 30 nM to 0.1235 nM, or 3-fold serially diluted from 10 nM to 0.0412 nM) were subsequently added to the wells in a volume of 100 μL. Anti-human CD40 antibodies BMK4 and BMK5 were used as positive controls. Human IgG1 and IgG2 isotype antibodies were used as isotype controls. The plates were incubated at 37° C., 5% $CO_2$ for 3 days. The supernatants were collected for IL-12p40 measurement by ELISA, and the cell pellets were harvested to detect the expression of CD80, CD86, CD83 and/or CD54 by FACS. The experiment was performed three times and all samples were tested in triplicates.

Human IL-12p40 secretion was measured by ELISA using Human IL-12 (p40) ELISA Set Kit as follow: Recombinant human IL-12p40 was used as standards. The serial concentrations 8, 4, 2, 1, 0.5, 0.25, 0.125, 0.0625 and 0.03125 ng/mL was used for standard curve. The plates were pre-coated with 50 μL of capture antibody specific for human IL-12p40 at a dilution ratio of 1:250 in coating buffer, then sealed the plates and incubated at 4° C. overnight. Next day, the plates were washed using 1×PBST for one time. After blocking with 1×PBS/2% BSA for 1 hour, 50 μL of standards or samples were pipetted into each well and incubated for 2 hours at an ambient temperature. After incubation, the plates were washed using 1×PBST for 3 times. Following removal of unbound substances, added working detector (biotinylated detection antibody and streptavidin-HRP at dilution ratio of 1:250 in 1×PBS/2% BSA) to the wells and incubated the plates at ambient temperature for one hour. After incubation, the plates were washed using 1×PBST for 6 times. The color was developed by dispensing 50 μL of TMB substrate solution, and the reaction was stopped by 50 μL of 2M HCl. The absorbance was read at 450 nm and 540 nm using a microplate spectrophotometer (M5e). The concentration of IL-12p40 in supernatant was back-calculated from the standard curve using the software SoftMax Pro built in M5e. GraphPad Prism was used to plot the log of antibody concentration (x-axis) versus IL-12p40 concentration (y-axis). The sigmoidal curve was fitted using four-parameter dose-response curve model.

The expression of CD80, CD86, CD83 and CD54 was measured by FACS using corresponding commercial fluorescent antibodies. The cells were transferred from the culture plates to FACS plates, and washed once using 1×PBS/1% BSA for one time. The fluorescent antibodies were 20- (for CD83) or 100-fold (for CD80, CD86 and CD54) diluted in 1×PBS/1% BSA and added to cells at 100 μL/well. The plates were incubated at 4° C. in dark for 1 hour. The cells were then washed and re-suspended in 1×PBS/1% BSA. MFI of the cells was measured by a flow cytometer and analyzed by FlowJo. GraphPad Prism was used to plot the log of antibody concentration (x-axis) versus MFI (y-axis). The sigmoidal curve was fitted using four-parameter dose-response curve model.

Figure 11:
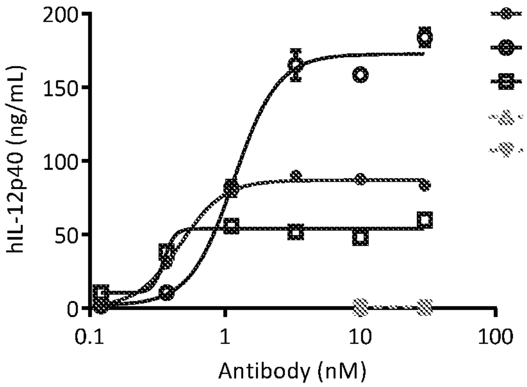
FIGS. 11-15 illustrate the result of IL-12p40 secretion (FIG. 11), CD80 (FIG. 12), CD86 (FIG. 13), CD54 (FIG. 14) and CD83 (FIG. 15) expression induced by W3525-1.9.16-P5-uIgG2K in in vitro DC activation assay.
Figure 12:
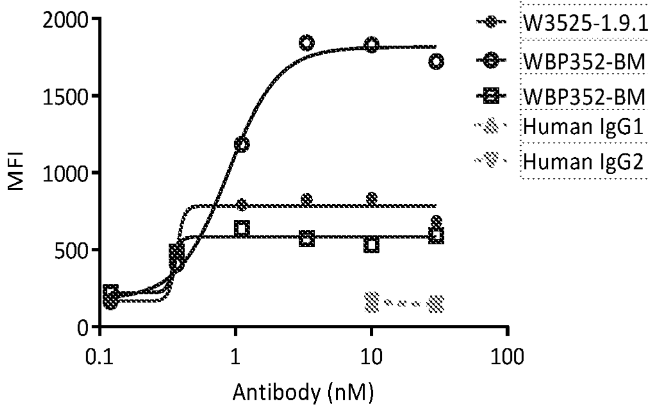
Figure 13:
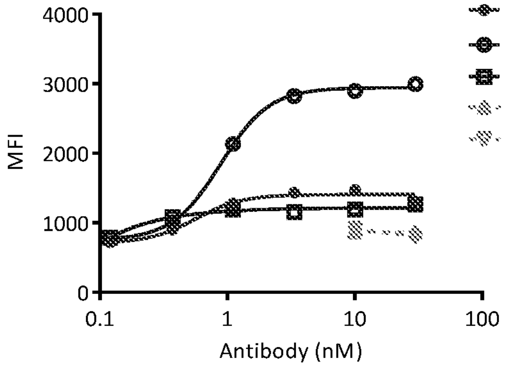
Figure 14:
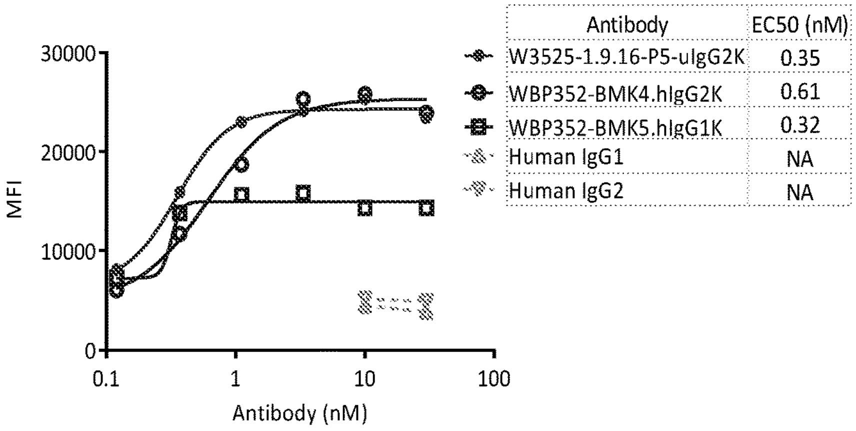
Figure 15:
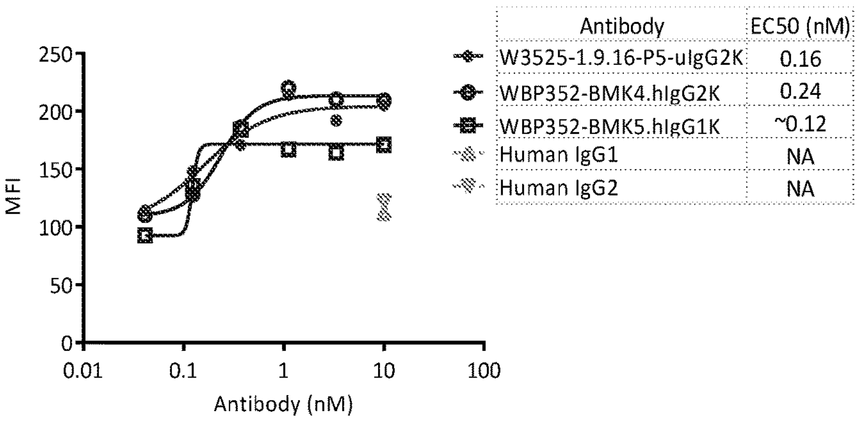

CD40 is expressed on APCs like monocytes and dendritic cells. CD40 ligation of monocytes and dendritic cells by CD40L or CD40-agonistic antibodies results in the secretion of multiple cytokines (such as IL-12), as well as up-regulation of activation markers (such as CD80, CD86, CD54 and CD83). The result of IL-12p40 secretion induced by W3525 is shown in FIG. 11. The results of CD80, CD86, CD54 and CD83 expression are shown in FIGS. 12, 13, 14 and 15. The potency data for IL-12p40 release and CD80, CD86, CD54 and CD83 expression are summarized in Table 9. Compared to BMK4, W3525 can induce moderate level of IL-12p40 secretion, as well as CD80 and CD86 up-regulation.

TABLE 9

Potency of antibodies in in vitro DC activation assay

| Antibody | IL-12p40 release $EC_{20}$ (nM) | IL-12p40 release $EC_{50}$ (nM) | IL-12p40 release $EC_{90}$ (nM) | CD80 expression $EC_{20}$ (nM) | CD80 expression $EC_{50}$ (nM) | CD80 expression $EC_{90}$ (nM) | CD86 expression $EC_{20}$ (nM) | CD86 expression $EC_{50}$ (nM) | CD86 expression $EC_{90}$ (nM) |
|---|---|---|---|---|---|---|---|---|---|
| W3525 | 0.28 | 0.47 | 1.1 | 0.32 | 0.37 | 0.46 | 0.31 | 0.56 | 1.4 |
| BMK4 | 0.69 | 1.2 | 2.6 | 0.49 | 0.88 | 2.2 | 0.48 | 0.88 | 2.3 |
| BMK5 | 0.31 | 0.35 | 0.43 | 0.30 | 0.35 | 0.41 | NA | NA | NA |

| Antibody | CD54 expression $EC_{20}$ (nM) | CD54 expression $EC_{50}$ (nM) | CD54 expression $EC_{90}$ (nM) | CD83 expression $EC_{20}$ (nM) | CD83 expression $EC_{50}$ (nM) | CD83 expression $EC_{90}$ (nM) |
|---|---|---|---|---|---|---|
| W3525 | 0.19 | 0.35 | 0.96 | 0.058 | 0.16 | 0.78 |
| BMK4 | 0.26 | 0.61 | 2.4 | 0.14 | 0.24 | 0.57 |
| BMK5 | 0.28 | 0.32 | 0.39 | 0.11 | 0.12 | 0.15 |

3.11 Antibody-Dependent Cell-Mediated Cytotoxicity Assay (ADCC)

In order to test the ADCC activity of W3525 on CD40 positive blood cell, CD40-expressing B cells were used as target cells and Jurkat-NFAT-CD16.A5 were used as the effector cells. Human primary B cells were isolated from human PBMCs by magnetic selection using human CD19 MicroBeads according to the manufacturer's protocol. The CD40 expression on human primary B cells was tested by FACS. Freshly isolated human B cells were plated in 96-well plates at a density of $4\times10^4$ cells/well in a volume of 50 μL. Then, various concentrations of testing antibodies (8-fold serially diluted from 200 nM to 0.0001 nM) were added to the wells in a volume of 50 μL. Anti-human CD40 antibodies BMK4 and BMK5 were used as positive controls. Human IgG1 and IgG2 isotype antibodies were used as isotype controls. And then, 50 μL of Jurkat-NFAT-CD16.A5 cells were added to the wells at the effector/target ratio of 2:1. The plate was kept at 37° C. in a 5% $CO_2$ incubator for about 5 hours. Antibody biological activity in ADCC was quantified through the luciferase produced as a result of NFAT pathway activation. The luciferase activity in the effector cells was quantified by One-Glo, and was read using a microplate spectrophotometer (Envision). GraphPad Prism was used to plot the log of antibody concentration (x-axis) versus fold change of luciferase intensity (y-axis). The sigmoidal curve was fitted using four-parameter dose-response curve model. All samples were tested in duplicates.

Figure 16:
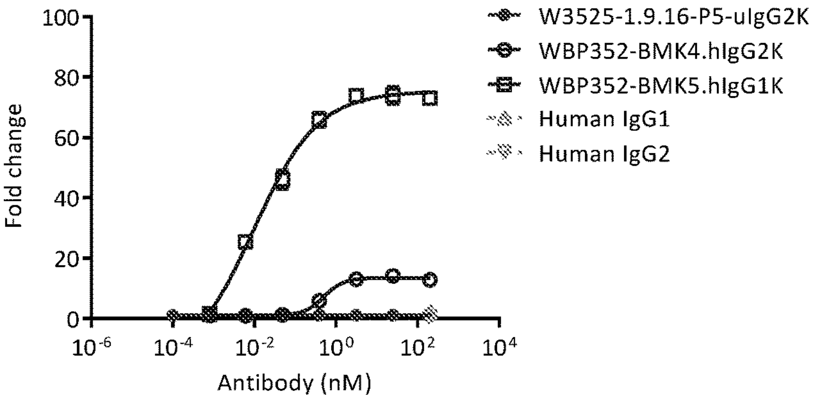
FIG. 16 illustrates the ADCC effect of the antibodies on human primary B cells.

CD40 is not only expressed on tumor cells such as B cell lymphoma, melanoma and carcinomas, but also wildly expressed on many kinds of normal cells such as monocytes, DCs and B cells, so we evaluated the ADCC activity of W3525 on human primary B cells. CD40 expression was confirmed by FACS on human B cells. The result of ADCC assay is shown in FIG. 16. The result shows that BMK5, the Fc backbone of which is human IgG1, can induce ADCC effect effectively on human B cells in a dose-dependent manner. However, W3525 and BMK4, which are in human IgG2 format, didn't or weakly mediate ADCC activity on human B cells. The result indicates that W3525 will not likely trigger ADCC on CD40 positive B cells.

In cancer treatment, the main mechanism of CD40-agonistic antibodies is to license APC to induce anti-tumor T cell response, not requiring CD40 expression on the tumor cells. However, the IgG1 antibody will induce Fc effector functions such as ADCC on CD40-expressing DCs and B cells, which may decrease the antitumor response. Actually, a decrease of B-cell count has been observed in the clinical trials. W3525 is a human IgG2 anti-CD40 antibody, avoiding the potential damage to CD40 positive normal cells.

3.12 Cytokine Release Assay

As an agonistic antibody, the most frequently reported adverse events of anti-CD40 antibody in clinical trials was cytokine release syndrome (CRS). The cytokine release assay was aimed to assess the cytokine release profile of W3525 in soluble condition using human PBMC without other stimulation.

Human PBMCs were freshly isolated from healthy donors using Ficoll-Paque PLUS gradient centrifugation, or purchased from PBMC vendor. The purified PBMCs were added in each well at a density of $1\times10^5$ cells/100 μL/well. W3525 and the other antibodies were added to the plate at 100 μL/well at working concentration of 66.7 nM. Anti-CD28 antibody TGN1412 was used as a positive control, and human IgG1 and IgG2 isotype antibodies were used as isotype controls. LPS was added at working concentration of 1 μg/mL. The plates were incubated at 37° C., 5% $CO_2$ for two days. The supernatant was collected and stored at −80° C. until ready for detection.

After collecting 10 sets of samples, the cytokines IL-2, IL-4, IL-6, IL-10, TNF, IFN-γ and IL-17A were measured using Cytometric Bead Array (CBA) Human Th1/Th2/Th17 Cytokine Kit according to manufacturer's protocol. The kit includes seven cytokine pre-captured beads (IL-2, IL-4, IL-6, IL-10, TNF, IFN-γ and IL-17A), seven cytokines pre-mixed standards, PE-conjugated detection antibodies and washing buffer. The CBA kit uses bead array technology to simultaneously detect multiple cytokine proteins in research samples. During the assay procedure, the cytokine capture beads and the recombinant standards or unknown samples were mixed and incubated with the PE-conjugated detection antibodies to form sandwich complexes. The intensity of PE fluorescence of each sandwich complex reveals the concentration of that cytokines. After acquiring samples on flow cytometer, the concentration of each cytokine can be quantitated according to the standard curves.

We have investigated whether the in vitro cytokine release assay is predictive of the ability of W3525 to activate PBMCs without triggering a release of multiple cytokines. The in vitro cytokine release assay was done to identify the potential hazard for cytokine release. W3525 was assessed for cytokine release in human PBMC in soluble format. This assay was performed using 10 donors' PBMC. Anti-CD28 antibody TGN1412 and LPS were used as positive control; and human IgG1 and IgG2 isotype antibody were used as isotype control. The standard curves were plot on the log-log graph paper, with cytokine concentration on the x-axis and MFI on the y-axis. The best fit standard curves were drawn through the standard points using GraphPad Prism. The concentration of each cytokine is shown in Table 10. The results show that treatment with W3525 alone did not stimulate human PBMC to release cytokines IL-2, IL-4, IL-6, IL-10, TNF, IFN-γ and IL-17A in great quantities. However, BMK4, which had a problem of cytokine release syndrome in clinical trials, induced much higher levels of cytokines production, such as IL-2, IL-4, IL-6 and TNF. All values are shown in Mean±SEM.

TABLE 10

Cytokine production in in vitro cytokine release assay

| Ab | IL-2 (pg/mL) | IL-4 (pg/mL) | IL-6 (pg/mL) | IL-10 (pg/mL) | TNF (pg/mL) | IFN-γ (pg/mL) | IL-17A (pg/mL) |
|---|---|---|---|---|---|---|---|
| W3525 | 4.7 ± 0.7 | 8.7 ± 2.3 | 1287.2 ± 609.3 | 6.7 ± 3.0 | 31.9 ± 11.1 | 29.1 ± 10.1 | 22.1 ± 10.7 |
| BMK4 | 9.0 ± 1.8 | 26.6 ± 10.1 | 1616.1 ± 743.0 | 13.7 ± 5.7 | 88.8 ± 24.4 | 85.3 ± 30.6 | 31.7 ± 16.6 |
| BMK5 | 7.6 ± 3.8 | 31.0 ± 16.7 | 1155.3 ± 604.4 | 6.1 ± 3.3 | 45.9 ± 17.8 | 22.1 ± 6.6 | 79.0 ± 49.9 |
| TGN1412 | 3.9 ± 0.3 | 24.5 ± 8.7 | 6147.8 ± 1768.6 | 21.2 ± 6.2 | 601.6 ± 234.6 | 4112.8 ± 2295.5 | 35.2 ± 15.6 |
| LPS | 14.1 ± 8.6 | 79.8 ± 24.7 | 12901.3 ± 1587.6 | 176.0 ± 61.6 | 679.7 ± 240.7 | 388.4 ± 123.3 | 53.0 ± 30.2 |
| Human IgG1 | 7.3 ± 1.8 | 7.2 ± 2.3 | 1289.1 ± 559.7 | 13.3 ± 8.3 | 40.9 ± 13.8 | 152.1 ± 64.9 | 68.9 ± 42.8 |
| Human IgG2 | 4.3 ± 0.5 | 9.1 ± 2.0 | 842.0 ± 406.3 | 6.0 ± 2.7 | 11.6 ± 3.5 | 155.7 ± 95.3 | 43.4 ± 32.0 |
| No Ab | 5.2 ± 0.8 | 18.3 ± 9.5 | 1346.1 ± 590.9 | 16.3 ± 8.8 | 28.0 ± 8.2 | 62.2 ± 23.3 | 84.8 ± 33.1 |

Example 4

In Vivo Characterization of W3525 Antibody 4.1 In Vivo Efficacy Study of Antibodies in MC38 Murine Colon Carcinoma Model in CD40 Humanized Mice In order to investigate the anti-tumor activity of W3525 on CD40 negative tumor model, human CD40 transgenic CD40-Hu mice (Shanghai Model Organisms) were used for tumor cell inoculation. CD40-Hu mice were subcutaneously injected with wild type MC38 tumor cells ($1\times10^5$) suspended in 0.1 mL DPBS (Dulbecco's Phosphate Buffered Saline) in the right front flank for tumor development. Tumor-bearing animals were randomly enrolled into six study groups when the mean tumor size reached about 80 $mm^3$. Each group consisted of 8 mice. The study design in shown Table 12. All antibodies were intraperitoneally administrated to tumor-bearing mice at a frequency of twice per week. Body weight and tumor volume were measured twice per week. Mice were euthanized according to pre-defined health criteria and the study was terminated twenty-five days post the first dosing.

TABLE 12

Study design of in vivo MC38 model

| Group | Test articles | No. of animals | Dosage | Dosing route | Dosing frequency |
|---|---|---|---|---|---|
| G1 | Human IgG2 | 8 | 10 mg/kg | i.p. | BIW × 3 w |
| G2 | W3525 | 8 | 10 mg/kg | i.p. | BIW × 3 w |
| G3 | W3525 | 8 | 1 mg/kg | i.p. | BIW × 3 w |

TABLE 12-continued

Study design of in vivo MC38 model

| Group | Test articles | No. of animals | Dosage | Dosing route | Dosing frequency |
|---|---|---|---|---|---|
| G4 | W3525 | 8 | 0.1 mg/kg | i.p. | BIW × 3 w |
| G5 | BMK4 | 8 | 10 mg/kg | i.p. | BIW × 3 w |
| G6 | BMK4 | 8 | 1 mg/kg | i.p. | BIW × 3 w |

Figure 17:
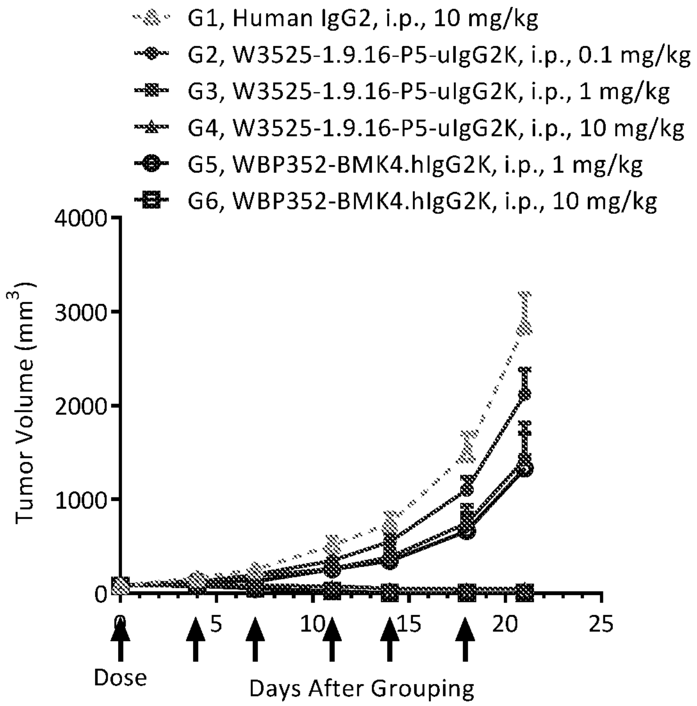
FIGS. 17-18 illustrate the tumor growth inhibition result (FIG. 17) and body weight change result (FIG. 18) of antibodies in MC38 murine colon carcinoma model in CD40 humanized mice. The arrows indicate the dosing days.

The tumor growth inhibition (TGI) was calculated and analyzed at the best therapeutic time-point (21 days post grouping). The results of tumor volume are shown in FIG. 17 and summarized in Table 13 and Table 14.

TABLE 13

Summary of tumor volume

| | Tumor Volume ($mm^3$)[a] | | | | | |
|---|---|---|---|---|---|---|
| Days post grouping | Human IgG2 | W3525, 10 mg/kg | W3525, 1 mg/kg | W3525, 0.1 mg/kg | BMK4, 10 mg/kg | BMK4, 1 mg/kg |
| 0 | 80 ± 5 | 80 ± 6 | 80 ± 5 | 80 ± 5 | 80 ± 6 | 80 ± 5 |
| 4 | 160 ± 21 | 90 ± 16 | 120 ± 25 | 120 ± 13 | 77 ± 7 | 132 ± 20 |
| 7 | 252 ± 42 | 86 ± 26 | 178 ± 47 | 196 ± 22 | 53 ± 5 | 125 ± 30 |
| 11 | 511 ± 81 | 76 ± 32 | 262 ± 70 | 347 ± 43 | 24 ± 4 | 255 ± 71 |
| 14 | 741 ± 106 | 52 ± 29 | 384 ± 103 | 550 ± 86 | 4 ± 4 | 344 ± 97 |
| 18 | 1,479 ± 218 | 43 ± 28 | 746 ± 184 | 1,099 ± 129 | 4 ± 4 | 661 ± 188 |
| 21 | 2,839 ± 348 | 52 ± 33 | 1,425 ± 387 | 2,120 ± 262 | 4 ± 4 | 1,327 ± 374 |
| 25 | / | 95 ± 55 | 2,149 ± 570 | 3,897 ± 569 | 10 ± 10 | 1,939 ± 772 |

Note:
[a]Mean ± SEM

TABLE 14

Tumor growth inhibition

| | | | Tumor volume ($mm^3$)[a] | | | | |
|---|---|---|---|---|---|---|---|
| Groups | Test articles | Dosages (mg/kg) | Before treatment | Day 21 post treatment | TGI (%) | P[b] | |
| G1 | Human IgG2 | 10 | 80 ± 5 | 2,839 ± 348 | — | — | — |
| G2 | W3525 | 10 | 80 ± 6 | 52 ± 33 | 101.01 | <0.001 | — |
| G3 | W3525 | 1 | 80 ± 5 | 1,425 ± 387 | 51.24 | 0.019 | — |
| G4 | W3525 | 0.1 | 80 ± 5 | 2,120 ± 262 | 26.06 | 0.118 | — |
| G5 | BMK4 | 10 | 80 ± 6 | 4 ± 4 | 102.75 | <0.001 | 0.171[c] |
| G6 | BMK4 | 1 | 80 ± 5 | 1,327 ± 374 | 54.79 | 0.012 | 0.859[d] |

Note:
[a]Mean ± SEM.
[b]Statistical analysis via independent sample t-test on mean tumor volume of the treatment group versus human IgG2 group on day 21 post grouping.
[c]Statistical analysis via independent sample t-test on mean tumor volume of G5 versus G2 on day 21 post grouping.
[d]Statistical analysis via independent sample t-test on mean tumor volume of G6 versus G3 on day 21 post grouping.

Note:

a, Mean±SEM.

b, Statistical analysis via independent sample t-test on mean tumor volume of the treatment group versus human IgG2 group on day 21 post grouping.

c, Statistical analysis via independent sample t-test on mean tumor volume of G5 versus G2 on day 21 post grouping.

d, Statistical analysis via independent sample t-test on mean tumor volume of G6 versus G3 on day 21 post grouping.

Figure 18:
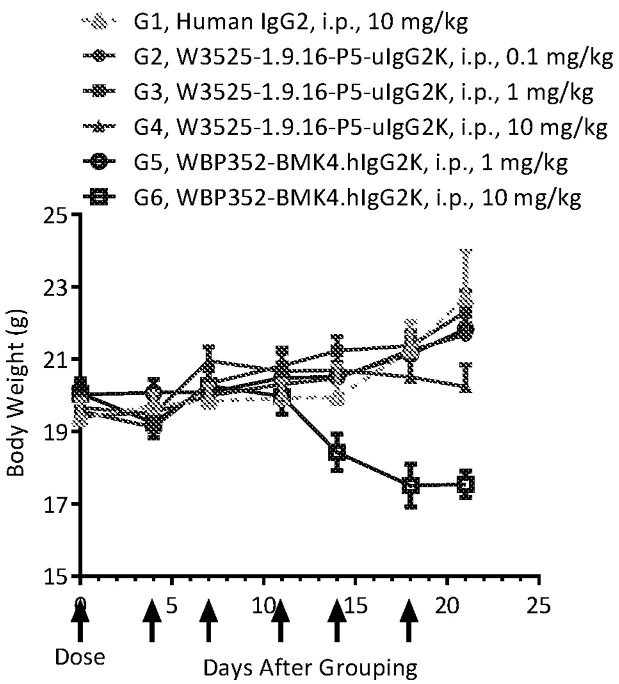

After the fourth injection, the body weight of animals in group WBP352-BMK4.hIgG4K, 10 mg/kg lost more than 10%, and all mice in this group were found lethargic and hypothermic, which lasted for more than one week until the end of the experiment. The results of mean body weight are shown in Table 15 and FIG. 18.

TABLE 15

Body weight change

| | | | Body Weight (g)[a] | | |
|---|---|---|---|---|---|
| Group | Test articles | Dosages (mg/kg) | Before treatment | Day 21 post grouping | Change (g) |
| G1 | Human IgG2 | 10 | 19.4 ± 0.5 | 22.7 ± 1.3 | +3.3 |
| G2 | W3525 | 10 | 19.7 ± 0.3 | 20.2 ± 0.6 | +0.5 |
| G3 | W3525 | 1 | 19.6 ± 0.4 | 22.3 ± 0.6 | +2.7 |
| G4 | W3525 | 0.1 | 19.4 ± 0.2 | 21.7 ± 0.3 | +2.3 |
| G5 | BMK4 | 10 | 20.1 ± 0.4 | 17.6 ± 0.4 | −2.5 |
| G6 | BMK4 | 1 | 20.0 ± 0.3 | 21.8 ± 0.8 | +1.8 |

Note:
[a]Mean ± SEM.

Twenty-one days after grouping, the TGI values of W3525 at 10 mg/kg and 1 mg/kg were 101.01% and 51.24%, respectively. The mean tumor volumes of these two groups were statistically significant different from human IgG2 group ($P<0.05$). The TGI value of W3525 at 0.1 mg/kg is 26.06%, but it had no statistical difference from human IgG2 group ($P>0.05$). These results indicated that W3525 has significant anti-tumor activity at the doses of 10 mg/kg and 1 mg/kg; and has limited tumor growth inhibition activity at the dose of 0.1 mg/kg.

The TGI values of BMK4 at 10 mg/kg and 1 mg/kg were 102.75% and 54.79%, respectively. Meanwhile, the mean tumor volume of these groups had statistically significant difference from that of human IgG2 group ($P<0.05$). The results indicate that the BMK4 reference antibody has significant anti-tumor activity at 10 mg/kg and 1 mg/kg.

However, more than 10% body weight loss was observed in the group of BMK4 10 mg/kg after the fourth dose, along with lethargy and hypothermia, and these signs lasted for more than one week, indicating the possible toxicity of this reference antibody at this dose level. In contrast, W3525 was well tolerated in the treated mice at all dose levels.

In summary, W3525 exhibited significant inhibition effect on tumor growth at the dose levels of both 1 mg/kg and 10 mg/kg, and the inhibition effect is dose-dependent. More importantly, all the grouped mice treated with W3525 were well tolerated, but the mice in high-dosed group showed intolerance to BMK4 treatment. W3525 mediates comparable anti-tumor activity to BMK4 (i.e. CP-870,893 of Pfizer), but induces lower toxicity, demonstrating the possibility to separate agonism and toxicity and the potential therapeutic utility in clinical trial of W3525.

4.2 In Vivo Efficacy Study of Antibodies in B16F10 Murine Melanoma Model in Humanized CD40 Mice This study was to evaluate the anti-tumor activity of W3525 in a cold tumor B16F10 melanoma model. Human CD40 transgenic CD40-Hu mice were subcutaneously injected with B16F10 tumor cells ($5\times10^6$) suspended in 0.1 mL DPBS in the right front flank for tumor development. Tumor-bearing animals were randomly enrolled into seven study groups when the mean tumor size reached about 60~80 $mm^3$. Each group consisted of 7 mice. The study design in shown Table 16. All antibodies were intraperitoneally administrated to tumor-bearing mice at a frequency of Q3d. Body weight and tumor volume were measured also Q3d. Mice were euthanized according to pre-defined health criteria and the study was terminated twenty-four days post the first dosing.

TABLE 16

Study design of in vivo B16F10 model

| Group | Test articles | No. of animals | Dosage | Dosing route | Dosing frequency |
|---|---|---|---|---|---|
| G1 | DPBS | 7 | / | i.p. | Q3d × 6 |
| G2 | W3525 | 7 | 1 mg/kg | i.p. | Q3d × 6 |
| G3 | W3525 | 7 | 3 mg/kg | i.p. | Q3d × 6 |
| G4 | W3525 | 7 | 10 mg/kg | i.p. | Q3d × 6 |
| G5 | APX005M | 7 | 1 mg/kg | i.p. | Q3d × 6 |
| G6 | APX005M | 7 | 3 mg/kg | i.p. | Q3d × 6 |
| G7 | APX005M | 7 | 10 mg/kg | i.p. | Q3d × 6 |

Figure 19:
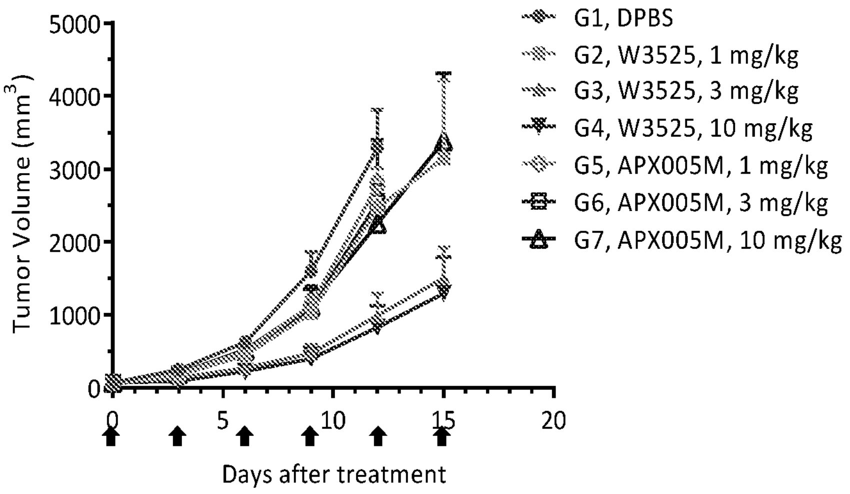
FIGS. 19-20 illustrate the tumor growth inhibition result (FIG. 19) and body weight change result (FIG. 20) of antibodies in B16F10 murine melanoma model in CD40 humanized mice. The arrows indicate the dosing days.

All mice were closely monitored for tumor growth and body weight during the entire experiment, with tumor size measured and recorded every three days. The tumor growth inhibition (TGI) was calculated and analyzed at the best therapeutic time-point (12 days post grouping). The results of tumor volume are shown in FIG. 19 and summarized in Table 17 and Table 18.

TABLE 17

Summary of tumor volume

| Days post grouping | DPBS | Tumor Volume ($mm^3$)[a] W3525, 1 mg/kg | W3525, 3 mg/kg | W3525, 10 mg/kg | APX005M, 1 mg/kg | APX005M, 3 mg/kg | APX005M, 10 mg/kg |
|---|---|---|---|---|---|---|---|
| 0 | 72 ± 8 | 72 ± 9 | 73 ± 9 | 72 ± 8 | 72 ± 8 | 73 ± 8 | 71 ± 9 |
| 3 | 250 ± 37 | 176 ± 28 | 136 ± 28 | 95 ± 22 | 192 ± 30 | 189 ± 39 | 195 ± 44 |
| 6 | 628 ± 84 | 448 ± 71 | 272 ± 60 | 227 ± 73 | 506 ± 64 | 490 ± 103 | 522 ± 112 |
| 9 | 1,603 ± 264 | 1,030 ± 163 | 474 ± 118 | 399 ± 152 | 1,135 ± 132 | 1,071 ± 325 | 1,123 ± 237 |
| 12 | 3,293 ± 524 | 2,467 ± 423 | 992 ± 295 | 831 ± 301 | 2,775 ± 233 | 2,547 ± 852 | 2,252 ± 534 |
| 15 | / | 3,144 ± 1072 | 1,507 ± 421 | 1,296 ± 496 | / | / | 3,387 ± 923 |

Note:
[a]Mean ± SEM

TABLE 18

Tumor growth inhibition

| Groups | Test articles | Dosages (mg/kg) | Tumor volume ($mm^3$)[a] Before treatment | Day 21 post treatment | TGI (%) | P[b] |
|---|---|---|---|---|---|---|
| G1 | DPBS | / | 72 ± 8 | 3,293 ± 524 | — | — |
| G2 | W3525 | 1 | 72 ± 9 | 2,467 ± 423 | 25.61 | 0.260 |
| G3 | W3525 | 3 | 73 ± 9 | 992 ± 295 | 71.45 | 0.002 |
| G4 | W3525 | 10 | 72 ± 8 | 831 ± 301 | 76.43 | 0.002 |
| G5 | APX005M | 1 | 72 ± 8 | 2,775 ± 233 | 16.05 | 0.363 |
| G6 | APX005M | 3 | 73 ± 8 | 2,547 ± 852 | 23.14 | 0.484 |
| G7 | APX005M | 10 | 71 ± 9 | 2,252 ± 534 | 32.25 | 0.222 |

Note:
[a]Mean ± SEM.
[b]Statistical analysis via independent sample t-test on mean tumor volume of the treatment group versus DPBS group on day 12 post grouping.

Figure 20:
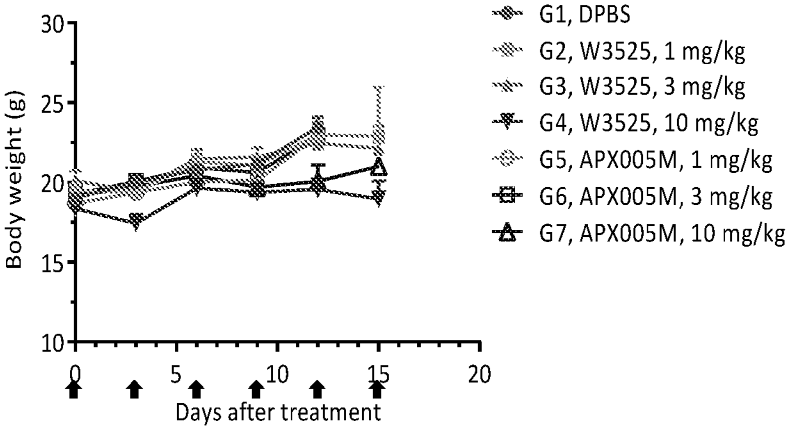

No obvious body weight loss was observed in this study. The results of mean body weight are shown in Table 19 and FIG. 20.

TABLE 19

Body weight change

| Group | Test articles | Dosages (mg/kg) | Body Weight (g)[a] Before treatment | Day 12 post grouping | Change (g) |
|---|---|---|---|---|---|
| G1 | DPBS | / | 19.0 ± 0.3 | 23.5 ± 0.6 | +4.5 |
| G2 | W3525 | 1 | 19.5 ± 0.4 | 23.0 ± 0.7 | +3.5 |
| G3 | W3525 | 3 | 20.1 ± 0.6 | 22.5 ± 0.7 | +2.4 |
| G4 | W3525 | 10 | 18.4 ± 0.5 | 19.6 ± 0.6 | +1.2 |
| G5 | APX005M | 1 | 18.7 ± 0.5 | 22.9 ± 0.8 | +4.2 |
| G6 | APX005M | 3 | 19.3 ± 0.3 | 22.9 ± 0.7 | +3.6 |
| G7 | APX005M | 10 | 19.2 ± 0.7 | 20.1 ± 1.0 | +0.9 |

Note:
[a]Mean ± SEM.

Figure 21:
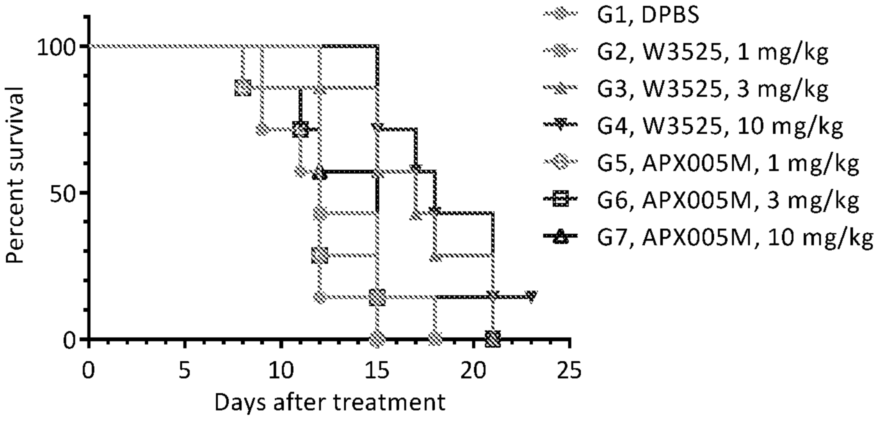
FIG. 21 illustrates the survival curve of mice bearing B16F10 melanoma after treatment with antibodies.

Survival of the mice was also determined and shown in FIG. 21. At the dosage of 3 and 10 mg/kg, W3525 prolonged the survival frequency of the mice implanted with B16F10 tumor.

Twelve days after grouping, the TGI values of W3525 at 3 mg/kg and 10 mg/kg were 71.45% and 76.43%, respectively. The mean tumor volumes of these two groups were statistically significant different from DPBS group (P<0.05). The TGI value of W3525 at 1 mg/kg is 25.61%, but it had no statistical difference from DPBS group (P>0.05). These results indicated that W3525 has significant anti-tumor activity at the doses of 10 mg/kg and 3 mg/kg; and has limited tumor growth inhibition activity at the dose of 1 mg/kg.

The TGI values of APX005M at 1 mg/kg, 3 mg/kg and 10 mg/kg were 16.05%, 23.14% and 32.25%, respectively. However, the mean tumor volume of these groups had no statistically significant difference from that of DPBS group (P<0.05). The results indicate that the reference antibody had little or weak anti-tumor activity at the three dosages.

The results demonstrating that, W3525 is more efficacious than APX005M in B16F10 tumor model, and W3525 not only inhibited tumor growth but also improved the survival of the tumor bearing mice.

Except for CP-870,893 and CDX-1140, the other CD40 agonistic antibodies are human IgG1, wild type or with modified Fc for enhancing specific FcγR binding ability, and generally require FcγR crosslinking for their agonistic activity. CP-870,893 is a fully human IgG2 with strong agonistic activity that has shown promising therapeutic efficacy in early clinical trials[15-16]. However, CP-870,893 has a limited therapeutic window with maximum tolerated dose of 0.2 mg/kg. Three dose-limited toxicity events were observed, including venous thromboembolism at 0.3 mg/kg, grade 3 headache at 0.3 mg/kg and grade 3 transient elevations in serum transaminases at 0.2 mg/kg. The most common adverse events associated with CP-870,893 treatment are cytokine release syndrome (grade 1 and grade 2) which included chills, rigors and fever (NCT02225002). Although accessible tumors are controlled by intratumoral injection of CP-870,893 (NCT02665416), this administration route has largely limited its clinical application. In contrast, CDX-1140, which is another CD40 agonistic antibody in human IgG2 format, although has good safety profiles in cynomolgus monkeys, has low affinity (~120 nM) to human CD40 and limited agonistic activity in activating DCs. ADC-1013 also showed good safety profile but with limited therapeutic efficacy when used as a single agent in clinical studies (NCT02379741). As for APX-005M, which is a human IgG1 with enhanced CD32b binding, though encouraging efficacy was observed in a phase 2 clinical trial (NCT03214250) for treating patients with previously untreated metastatic pancreatic adenocarcinoma, safety is also a big problem.

W3525-1.9.16-P5-uIgG2K is a fully human agonistic antibody with wild typed human IgG2 constant region. The antibody blocks CD40L binding to CD40, while CP-870,893 failed to block CD40L binding to CD40. It has been shown that CD40L-blocking antibodies tend to have more potent CD40 agonistic activity than CD40L-non-blocking antibodies[21].

Those skilled in the art will further appreciate that the present disclosure may be embodied in other specific forms without departing from the spirit or central attributes thereof.

In that the foregoing description of the present disclosure discloses only exemplary embodiments thereof, it is to be understood that other variations are contemplated as being within the scope of the present disclosure. Accordingly, the present disclosure is not limited to the particular embodiments that have been described in detail herein. Rather, reference should be made to the appended claims as indicative of the scope and content of the disclosure.

REFERENCES

[1] Jenkins R W, Barbie D A, Flaherty K T. Mechanisms of resistance to immune checkpoint inhibitors[J]. Br J Cancer. 2018, 118: 9-16.

[2] Ma B, Osborn M J, Avis S et al. Human antibody expression in transgenic rats: comparison of chimeric IgH loci with human VH, D and JH but bearing different rat C-gene regions[J]. J Immunol Methods. 2013, 400-401: 78-86.

[3] Bruggeemann M, Buelow R, Osborn M J et al. Polynucleotides encoding rodent antibodies with human idiotypes and animals comprising same[P]. 2014.

[4] Caux C, Massacrier C, Vanbervliet B et al. Activation of human dendritic cells through CD40 cross-linking[J]. J Exp Med. 1994, 180(4): 1263-1272.

[5] Clark E A. A Short History of the B-Cell-Associated Surface Molecule CD40[J]. Front Immunol. 2014, 5: 472.

[6] Kiener P A, Moran-Davis P, Rankin B M et al. Stimulation of CD40 with purified soluble gp39 induces proinflammatory responses in human monocytes[J]. J Immunol. 1995, 155(10): 4917-4925.

[7] Henn V, Steinbach S, Buchner K et al. The inflammatory action of CD40 ligand (CD154) expressed on activated human platelets is temporally limited by coexpressed CD40[J]. Blood. 2001, 98(4): 1047-1054.

[8] Yellin M J, Brett J, Baum D et al. Functional interactions of T cells with endothelial cells: the role of CD40L-CD40-mediated signals[J]. J Exp Med. 1995, 182(6): 1857-1864.

[9] Noelle R J, Roy M, Shepherd D M et al. A 39-kDa protein on activated helper T cells binds CD40 and transduces the signal for cognate activation of B cells[J]. Proc Natl Acad Sci USA. 1992, 89(14): 6550-6554.

[10] Grewal I S, Flavell R A. CD40 and CD154 in cell-mediated immunity[J]. Annu Rev Immunol. 1998, 16: 111-135.

[11] Rakhmilevich A L, Alderson K L, Sondel P M. T-cell-independent antitumor effects of CD40 ligation[J]. Int Rev Immunol. 2012, 31(4): 267-278.

[12] Loskog A S, Eliopoulos A G. The Janus faces of CD40 in cancer[J]. Semin Immunol. 2009, 21(5): 301-307.

[13] Matsuzawa A, Tseng P H, Vallabhapurapu S et al. Essential cytoplasmic translocation of a cytokine receptor-assembled signaling complex[J]. Science. 2008, 321 (5889): 663-668.
[14] Summers deLuca L, Gommerman J L. Fine-tuning of dendritic cell biology by the TNF superfamily[J]. Nat Rev Immunol. 2012; 12(5):339-351.
[15] Gladue R P, Paradis T, Cole S H et al. The CD40 agonist antibody CP-870,893 enhances dendritic cell and B-cell activity and promotes anti-tumor efficacy in SCID-hu mice[J]. Cancer Immunol Immunother. 2011, 60(7): 1009-1017.
[16] Vonderheide R H, Flaherty K T, Khalil M et al. Clinical activity and immune modulation in cancer patients treated with CP-870,893, a novel CD40 agonist monoclonal antibody[J]. J Clin Oncol. 2007, 25(7): 876-883.
[17] Bajor D L, Xu X, Torigian D A et al. Immune activation and a 9-year ongoing complete remission following CD40 antibody therapy and metastasectomy in a patient with metastatic melanoma[J]. Cancer Immunol Res. 2014, 2(11): 1051-1058.
[18] Nowak A K, Cook A M, McDonnell A M et al. A phase 1b clinical trial of the CD40-activating antibody CP-870, 893 in combination with cisplatin and pemetrexed in malignant pleural mesothelioma[J]. Ann Oncol. 2015, 26(12): 2483-2490.
[19] Mark O'Hara. A Phase 1b study of CD40 agonistic monoclonal antibody APX005M together with gemcitabine (Gem) and nab-paclitaxel (NP) with or without nivolumab (Nivo) in untreated metastatic ductal pancreatic adenocarcinoma (PDAC) patients (Abstract CT004). AACR 2019 Annual Meeting, University of Pennsylvania.
[20] Vitale L A, Thomas L J, He L Z et al. Development of CDX-1140, an agonist CD40 antibody for cancer immunotherapy[J]. Cancer Immunol Immunother. 2019, 68(2): 233-245.
[21] Barr T A, Heath A W. Functional activity of CD40 antibodies correlates to the position of binding relative to CD154[J]. Immunology. 2001, 102(1): 39-43.
[22] Johnson P, Challis R, Chowdhury F et al. Clinical and biological effects of an agonist anti-CD40 antibody: a Cancer Research UK phase I study[J]. Clin Cancer Res. 2015, 21(6): 1321-1328.
[23] Irenaeus S M M, Nielsen D, Ellmark P et al. First-in-human study with intratumoral administration of a CD40 agonistic antibody, ADC-1013, in advanced solid malignancies[J]. Int J Cancer. 2019, 145(5): 1189-1199.
[24] An H J, Kim Y J, Song D H, et al. Crystallographic and mutational analysis of the CD40-CD154 complex and its implications for receptor activation[J]. J Biol Chem. 2011, 286(13):11226-11235.

The invention claimed is:

1. An isolated antibody or an antigen-binding portion thereof that binds to CD40, wherein the isolated antibody or the antigen-binding portion thereof comprises:

a heavy chain CDR (HCDR)1 comprising SEQ ID NO: 1;

a HCDR2 comprising SEQ ID NO: 2;

a HCDR3 comprising SEQ ID NO: 3;

a light chain CDR (LCDR)1 comprising SEQ ID NO: 4 or 7;

a LCDR2 comprising SEQ ID NO: 5; and a LCDR3 comprising SEQ ID NO: 6.

2. The isolated antibody or the antigen-binding portion thereof of claim 1, wherein the isolated antibody or the antigen-binding portion thereof comprises:

(A) a heavy chain variable region (VH):

(i) comprising the amino acid sequence as set forth in SEQ ID NO: 8;

(ii) comprising an amino acid sequence that is at least 85% identical to SEQ ID NO: 8; and/or (B) a light chain variable region (VL):

(i) comprising the amino acid sequence as set forth in SEQ ID NO: 9 or 10;

(ii) comprising an amino acid sequence that is at least 85% identical to SEQ ID NO: 9 or 10.

3. The isolated antibody or the antigen-binding portion thereof of claim 1, wherein the isolated antibody further comprises a human IgG constant region.

4. The isolated antibody or the antigen-binding portion thereof of claim 3, wherein the human IgG constant region is a human IgG1 or IgG2 constant region.

5. The isolated antibody or the antigen-binding portion thereof of claim 4, wherein the human IgG constant region is a human IgG2 constant region.

6. The isolated antibody or the antigen-binding portion thereof of claim 3, wherein the human IgG constant region is wild-type or comprises one or more amino acid substitution(s) that alters the antibody-dependent cellular cytotoxicity (ADCC) or other effector functions.

7. The isolated antibody or the antigen-binding portion thereof of claim 1, wherein the antibody is an agonistic antibody against CD40.

8. The isolated antibody or the antigen-binding portion thereof of claim 1, wherein the antibody is a chimeric antibody or has fully human regions.

9. The isolated antibody or the antigen-binding portion thereof of claim 1, comprising a heavy chain comprising the amino acid sequence of SEQ ID NO: 14 and a light chain comprising the amino acid sequence of SEQ ID NO: 15.

10. A kit, comprising a container comprising the antibody or the antigen-binding portion thereof as defined in claim 1.

11. A pharmaceutical composition comprising the antibody or the antigen-binding portion thereof as defined in claim 3 and a pharmaceutically acceptable carrier.

12. An isolated nucleic acid molecule, comprising one or more nucleic acid sequences encoding the isolated antibody as defined in claim 1.

13. A vector comprising the nucleic acid molecule of claim 12.

14. A host cell comprising the vector of claim 13.

15. A method for producing the antibody or the antigen-binding portion thereof as defined in claim 1 comprising the steps of:

culturing a host cell comprising an expression vector(s) encoding the antibody or the antigen-binding portion thereof under suitable conditions;

expressing the antibody or the antigen-binding portion thereof; and harvesting the antibody or the antigen-binding portion thereof from the cell culture.

16. A method of boosting a CD40 related immune response against cancer cells in a subject, comprising administering to the subject the antibody or the antigen-binding portion thereof as defined in claim 3.

17. A method for inhibiting growth of tumor cells in a subject, comprising administering an effective amount of the antibody or the antigen-binding portion thereof as defined in claim 3 to the subject.

18. A method of treatment for cancer, comprising administering an effective amount of the antibody or the antigen-binding portion thereof as defined in claim 3 to a subject that has cancer.

19. The method of claim 18, wherein the cancer is selected from breast cancer, lung cancer, colon cancer, ovarian cancer, melanoma, bladder cancer, renal cell carcinoma, liver cancer, prostate cancer, stomach cancer, pancreatic cancer, NSCLC, non-Hodgkin's lymphoma, chronic lymphocytic leukemia, diffuse large B-cell lymphoma, and multiple myeloma.

20. The method of claim 19, wherein the cancer is colon cancer or melanoma.

* * * * *

SEQUENCE LISTING

```
<160> NUMBER OF SEQ ID NOS: 15

<210> SEQ ID NO 1
<211> LENGTH: 10
<212> TYPE: PRT
<213> ORGANISM: Artificial Sequence
<220> FEATURE:
<223> OTHER INFORMATION: HCDR1

<400> SEQUENCE: 1

Gly Asp Thr Val Ser Ser Tyr Gly Ile Ser
1               5                   10


<210> SEQ ID NO 2
<211> LENGTH: 17
<212> TYPE: PRT
<213> ORGANISM: Artificial Sequence
<220> FEATURE:
<223> OTHER INFORMATION: HCDR2

<400> SEQUENCE: 2

Gly Ser Ile Pro Phe Phe Gly Thr Pro Asn Tyr Ala Gln Lys Phe Gln
1               5                   10                  15

Gly


<210> SEQ ID NO 3
<211> LENGTH: 17
<212> TYPE: PRT
<213> ORGANISM: Artificial Sequence
<220> FEATURE:
<223> OTHER INFORMATION: HCDR3

<400> SEQUENCE: 3

Ala Arg Arg Gly Tyr Ser Tyr Gly His Tyr His Tyr Tyr Ala Met Asp
1               5                   10                  15

Val
```

<210> SEQ ID NO 4
<211> LENGTH: 16
<212> TYPE: PRT
<213> ORGANISM: Artificial Sequence
<220> FEATURE:
<223> OTHER INFORMATION: LCDR1,p5

<400> SEQUENCE: 4

Arg Ser Gly Gln Ser Leu Leu His Asn Asn Ala Tyr Asn Tyr Leu Asp
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: LCDR2

<400> SEQUENCE: 5

Leu Gly Ser Asn Arg Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: LCDR3

<400> SEQUENCE: 6

Met Gln Ala Leu Gln Thr Pro Leu Ser
1               5

<210> SEQ ID NO 7
<211> LENGTH: 16
<212> TYPE: PRT
<213> ORGANISM: Artificial Sequence
<220> FEATURE:
<223> OTHER INFORMATION: LCDR1

<400> SEQUENCE: 7

Arg Ser Gly Gln Ser Leu Leu His Asn Asn Gly Tyr Asn Tyr Leu Asp
1               5                   10                  15

<210> SEQ ID NO 8
<211> LENGTH: 126
<212> TYPE: PRT
<213> ORGANISM: Artificial Sequence
<220> FEATURE:
<223> OTHER INFORMATION: VH

<400> SEQUENCE: 8

Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Val Ser Ser Tyr
            20                  25                  30

Gly Ile Ser Trp Val Arg Gln Ala Pro Gly Gln Gly Leu Glu Trp Met
        35                  40                  45

Gly Gly Ser Ile Pro Phe Phe Gly Thr Pro Asn Tyr Ala Gln Lys Phe
    50                  55                  60

Gln Gly Arg Val Thr Phe Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Arg Arg Gly Tyr Ser Tyr Gly His Tyr His Tyr Tyr Ala
            100                 105                 110

Met Asp Val Trp Gly Gln Gly Thr Thr Val Thr Val Ala Ser
        115                 120                 125

<210> SEQ ID NO 9
<211> LENGTH: 112
<212> TYPE: PRT
<213> ORGANISM: Artificial Sequence
<220> FEATURE:
<223> OTHER INFORMATION: VL, p5

<400> SEQUENCE: 9

Asp Thr Val Met Thr Gln Ser Pro Leu Ser Leu Pro Val Thr Pro Gly
1               5                   10                  15

Glu Pro Ala Ser Ile Ser Cys Arg Ser Gly Gln Ser Leu Leu His Asn
            20                  25                  30

Asn Ala Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Ser Phe Gly Gly Gly Thr Lys Val Glu Ile Lys
            100                 105                 110

<210> SEQ ID NO 10
<211> LENGTH: 112
<212> TYPE: PRT
<213> ORGANISM: Artificial Sequence
<220> FEATURE:
<223> OTHER INFORMATION: VL, parent antibody

<400> SEQUENCE: 10

Asp Thr Val Met Thr Gln Ser Pro Leu Ser Leu Pro Val Thr Pro Gly
1               5                   10                  15

Glu Pro Ala Ser Ile Ser Cys Arg Ser Gly Gln Ser Leu Leu His Asn
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Ser Phe Gly Gly Gly Thr Lys Val Glu Ile Lys
            100                 105                 110

<210> SEQ ID NO 11
<211> LENGTH: 378
<212> TYPE: DNA
<213> ORGANISM: Artificial Sequence
<220> FEATURE:
<223> OTHER INFORMATION: VH

<400> SEQUENCE: 11
caggtgcagc tggtgcagtc tggggctgag gtgaagaagc ctgggtcctc ggtgaaggtc     60

```
tcctgcaagg cttctggaga caccgtcagc agctatggta tcagctgggt gcgacaggcc    120

cctggacaag ggcttgagtg gatgggaggg agcatccctt tctttggtac accaaactac    180

gcacagaagt tccagggcag agtcacgttt accgcggacg aatccacgag cacagcctac    240

atggagctga gcagcctgag atctgaggac acggccgtgt attactgtgc gagagcgaga    300

cgtggataca gctatggtca ctaccactac tacgctatgg acgtctgggg ccaagggacc    360

acggtcaccg tcgcctca                                                  378


<210> SEQ ID NO 12
<211> LENGTH: 336
<212> TYPE: DNA
<213> ORGANISM: Artificial Sequence
<220> FEATURE:
<223> OTHER INFORMATION: VL, p5

<400> SEQUENCE: 12

gatactgtga tgactcagtc tccactctcc ctgcccgtca cccctggaga gccggcctcc     60

atctcctgca ggtctggtca gagcctcctg cataataatg cgtacaacta tttggattgg    120

tacctgcaga agccagggca gtctccacag ctcctgatct atttgggttc taatcgggcc    180

tccggggtcc ctgacaggtt cagtggcagt ggatcaggca cagattttac actgaaaatc    240

agcagagtgg aggctgagga tgttggggtt tattactgca tgcaagctct acaaactcct    300

ctcagtttcg gcggagggac caaggtggag atcaaa                              336


<210> SEQ ID NO 13
<211> LENGTH: 336
<212> TYPE: DNA
<213> ORGANISM: Artificial Sequence
<220> FEATURE:
<223> OTHER INFORMATION: VL, parental antibody

<400> SEQUENCE: 13

gatactgtga tgactcagtc tccactctcc ctgcccgtca cccctggaga gccggcctcc     60

atctcctgca ggtctggtca gagcctcctg cataataatg gatacaacta tttggattgg    120

tacctgcaga agccagggca gtctccacag ctcctgatct atttgggttc taatcgggcc    180

tccggggtcc ctgacaggtt cagtggcagt ggatcaggca cagattttac actgaaaatc    240

agcagagtgg aggctgagga tgttggggtt tattactgca tgcaagctct acaaactcct    300

ctcagtttcg gcggagggac caaggtggag atcaaa                              336


<210> SEQ ID NO 14
<211> LENGTH: 452
<212> TYPE: PRT
<213> ORGANISM: Artificial Sequence
<220> FEATURE:
<223> OTHER INFORMATION: heavy chain, p5

<400> SEQUENCE: 14

Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Val Ser Ser Tyr
            20                  25                  30

Gly Ile Ser Trp Val Arg Gln Ala Pro Gly Gln Gly Leu Glu Trp Met
        35                  40                  45

Gly Gly Ser Ile Pro Phe Phe Gly Thr Pro Asn Tyr Ala Gln Lys Phe
    50                  55                  60
```

```
Gln Gly Arg Val Thr Phe Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Arg Arg Gly Tyr Ser Tyr Gly His Tyr His Tyr Tyr Ala
            100                 105                 110

Met Asp Val Trp Gly Gln Gly Thr Thr Val Thr Val Ala Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Asn Phe Gly Thr Gln Thr Tyr Thr
        195                 200                 205

Cys Asn Val Asp His Lys Pro Ser Asn Thr Lys Val Asp Lys Thr Val
    210                 215                 220

Glu Arg Lys Cys Cys Val Glu Cys Pro Pro Cys Pro Ala Pro Pro Val
225                 230                 235                 240

Ala Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Phe Arg Val Val Ser Val Leu Thr Val Val His Gln Asp Trp Leu Asn
305                 310                 315                 320

Gly Lys Glu Tyr Lys Cys Lys Val Ser Asn Lys Gly Leu Pro Ala Pro
                325                 330                 335

Ile Glu Lys Thr Ile Ser Lys Thr Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Met Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450
```

<210> SEQ ID NO 15
<211> LENGTH: 219
<212> TYPE: PRT

-continued

```
<213> ORGANISM: Artificial Sequence
<220> FEATURE:
<223> OTHER INFORMATION: p5, light chain

<400> SEQUENCE: 15

Asp Thr Val Met Thr Gln Ser Pro Leu Ser Leu Pro Val Thr Pro Gly
1               5                   10                  15

Glu Pro Ala Ser Ile Ser Cys Arg Ser Gly Gln Ser Leu Leu His Asn
            20                  25                  30

Asn Ala Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Ser Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```